(12) United States Patent
Wilson

(10) Patent No.: US 6,562,015 B1
(45) Date of Patent: May 13, 2003

(54) GARMENT WITH BARRIER DEVICE AND APPARATUS AND METHOD FOR PRODUCING SUCH GARMENT

(75) Inventor: Lorraine Dawn Wilson, Federal Way, WA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 09/066,555

(22) Filed: Apr. 28, 1998

Related U.S. Application Data

(62) Division of application No. 08/521,397, filed on Aug. 28, 1995, now Pat. No. 5,766,411.

(51) Int. Cl.$^7$ ................................................ A61F 13/15
(52) U.S. Cl. .................... 604/385.01; 604/385.101; 604/385.04; 604/385.28
(58) Field of Search ................. 604/385.2, 378, 604/380, 383, 384, 385.01, 385.101, 385.27, 385.24, 386, 393, 394, 385.28, 385.08, 385.04, 358, 398

(56) References Cited

U.S. PATENT DOCUMENTS

| | | | | |
|---|---|---|---|---|
| 2,575,164 A | * | 11/1951 | Donovan | 128/287 |
| 4,846,825 A | * | 7/1989 | Enloe et al. | 604/385.01 |
| 5,207,662 A | * | 5/1993 | James | 604/385.02 |
| 5,304,159 A | * | 4/1994 | Tanji et al. | 604/385.2 |
| 5,304,160 A | * | 4/1994 | Igaue et al. | 604/385.2 |
| 5,342,342 A | * | 8/1994 | Kitaoka | 604/385.2 |
| 5,397,318 A | * | 3/1995 | Dreier | 604/385.2 |
| 5,417,680 A | * | 5/1995 | Kimura et al. | 604/385.02 |
| 5,429,632 A | * | 7/1995 | Tanji et al. | 604/385.2 |
| 5,439,459 A | * | 8/1995 | Tanji et al. | 604/385.2 |
| 5,576,091 A | * | 11/1996 | Zajaczkowski et al. | 428/192 |
| 5,634,917 A | * | 6/1997 | Fujioka et al. | 604/385.2 |
| 5,752,946 A | * | 5/1998 | Boberg et al. | |
| 5,810,799 A | * | 9/1998 | Slater | 604/385.01 |
| 6,007,528 A | * | 12/1999 | Osborn, III | 604/387 |
| 6,056,733 A | * | 5/2000 | Kielpikowski | 604/385.2 |
| 6,254,583 B1 | * | 7/2001 | Coates | 604/385.14 |

* cited by examiner

Primary Examiner—Weilun Lo
Assistant Examiner—Michael Bogart
(74) Attorney, Agent, or Firm—Patrick A. Doody; Christopher C. Campbell; Hunton & Williams

(57) ABSTRACT

A disposable absorbent garment includes a backsheet, a liner sheet and an absorbent core disposed therebetween. The backsheet and liner sheets are shaped to form a pair of spaced-apart leg openings with a front waist area, a rear waist and a central crotch area. A pair of ribbons are disposed in opposing curved contours along at least the front and rear areas of the garment and optionally extend through the crotch area of the garment to form a generally oval-shaped exudate containment region about the crotch area of the garment. Each ribbon is fastened to the garment along one longitudinal ribbon edge to form free ribbon edges which rise from the garment to provide a raised barrier.

24 Claims, 13 Drawing Sheets

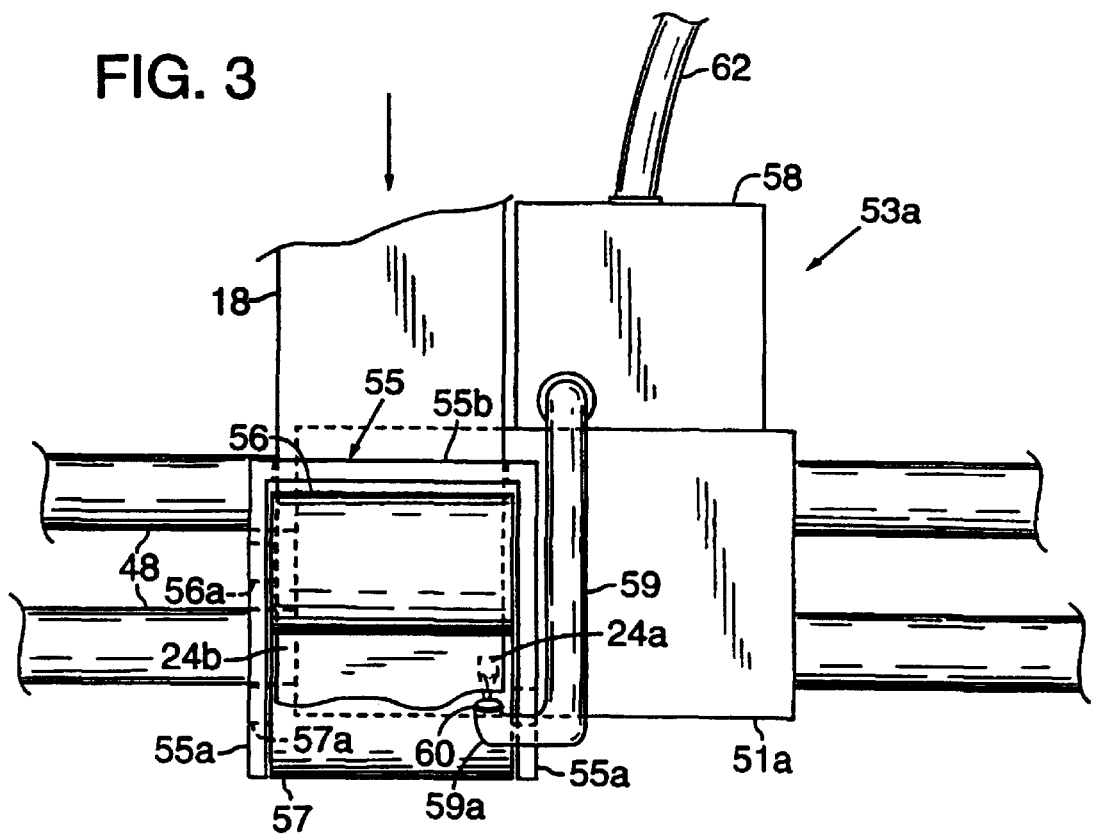
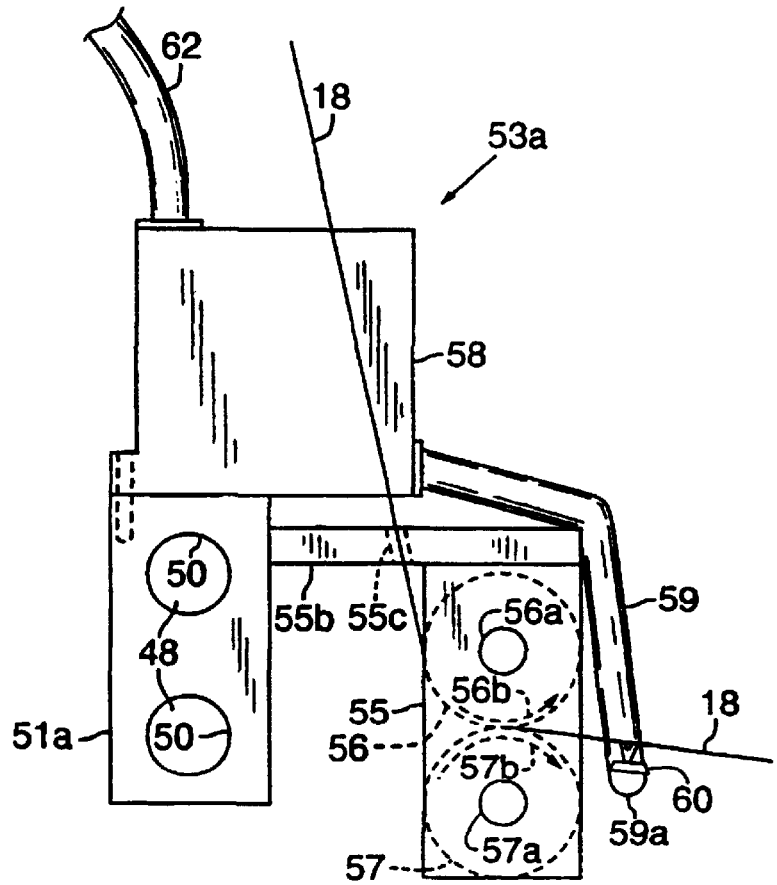

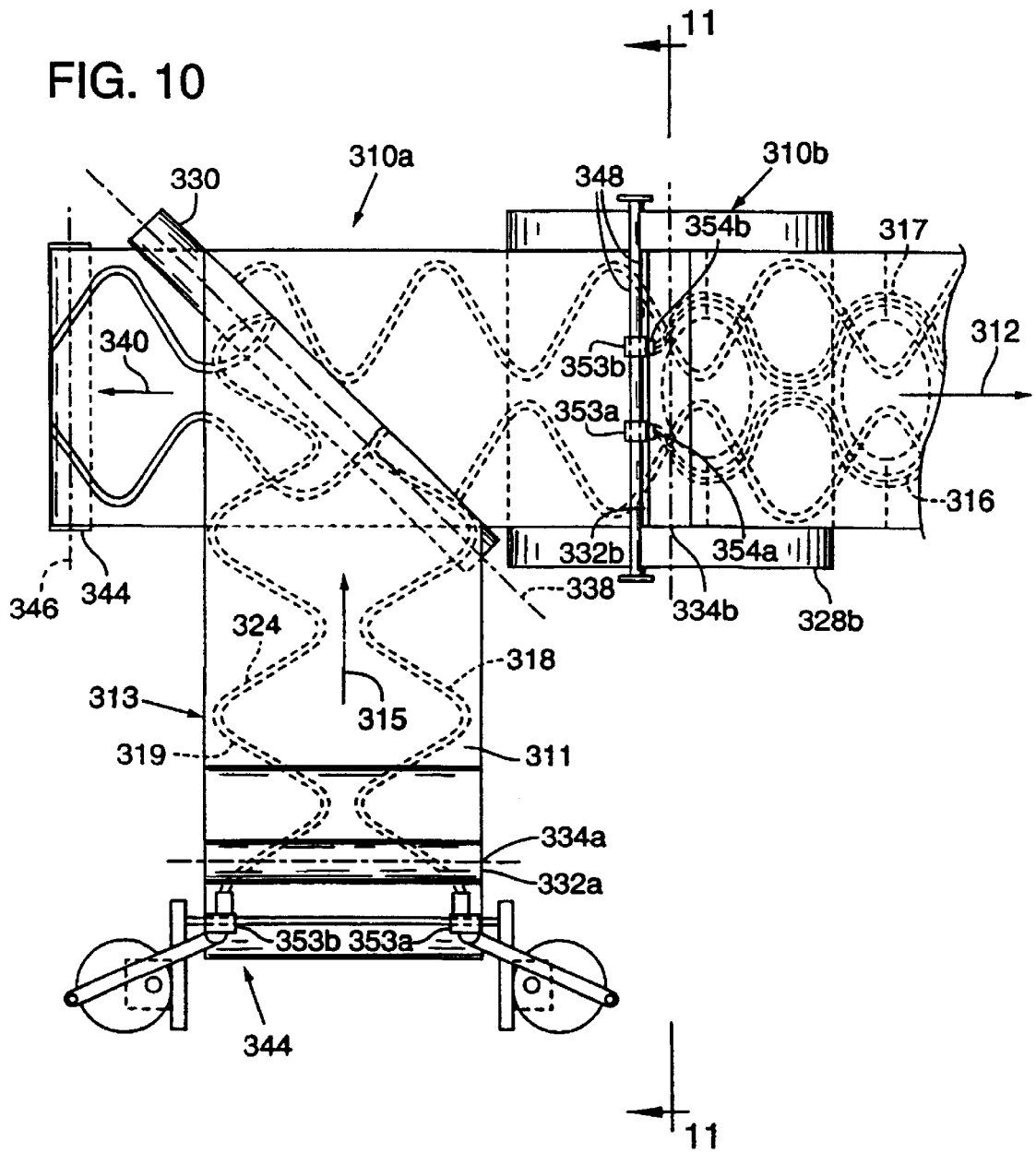

GARMENT WITH BARRIER DEVICE AND APPARATUS AND METHOD FOR PRODUCING SUCH GARMENT

This application is a divisional application of U.S. patent application Ser. No. 08/521,397, filed Aug. 28, 1995, now U.S. Pat. No. 5,766,411.

FIELD OF THE INVENTION

The present invention is directed to disposable absorbent garments with raised exudate barriers, and to apparatus and method for producing such garments.

BACKGROUND AND SUMMARY OF THE INVENTION

The manufacture of disposable absorbent garments, such as children's diapers and training pants, is well known in the art. Although elasticized waist bands and elasticized leg openings exhibit enhanced containment of bodily exudates, they have not been entirely successful in eliminating leakage. For instance, when a wearer voids, exudate may be released too quickly for complete absorption by the garment, leading to wicking and overflow of exudate from the garment to clothing or bedding contacting the edge of the garment.

To address this problem, "barrier devices" such as target regions, inner leg gathers and end caps have been provided on the inner liner of some absorbent garments to better confine exudates.

Conventional "target regions" are formed by layering a relatively impermeable liner sheet having a cut-out target region over a relatively absorbent material layer. Such target region construction helps to confine the absorption of exudates to a desired region of the garment. However, such target regions are not completely effective at containing rapidly exuded wastes.

Other conventional barrier devices forming raised barriers, such as some end caps and inner leg gathers, may be integrally formed by appropriately folding garment inner liner material to provide a raised barrier. Alternatively, such barriers may be constructed of elasticized flaps that are adhered onto garment inner liner material. End caps are usually disposed adjacent and parallel to the waist regions of a garment, and inner leg gathers are usually disposed lateral of the waist regions along the leg openings of a garment.

Conventional end cap and inner leg gather barrier devices provide improved management of exudates by containing, or at least slowing, the spread of exudates. Such containment permits the garment absorbent material to effectively absorb the exudates well away from the edges of the garment.

In spite of such advantages, conventional barrier devices are still somewhat less than satisfactory in terms of production expense and waste management effectiveness. For instance, the provision of end caps or inner leg gathers alone on garments does not offer complete containment of exudates. While the provision of both end caps and inner leg gathers on garments offers improved containment, the end caps and inner leg gathers are each formed separately on garments, which requires complex machinery which often cannot operate at desirable high production rates. Thus, the unit production cost of such garments tends to be high. Moreover, even if conventional end caps and inner leg gathers are both provided on garments, leakage can still occur between the gathers and the caps.

In light of the above, it is an object of the present invention to provide a garment with an improved barrier device, and to provide a machine and method for making such a garment.

One more object of the present invention is to provide a machine that applies an improved unitary inner leg gather and end cap to garment material at high working speeds.

In accordance with the present invention, a disposable absorbent garment is provided with a unitary raised end cap and inner leg gather barrier device. The disposable absorbent garment is provided with a backsheet, and a liner sheet overlying the backsheet. The backsheet and liner sheet are shaped to form a pair of spaced-apart leg openings, with a front waist area, a rear waist area, and a central crotch area. A pair of ribbons are disposed in opposing curved contours along front and rear areas of the garment to form a generally oval-shaped exudate containment region about the crotch area of the garment. Each ribbon is fastened to the garment along one longitudinal ribbon edge to form a "free" ribbon edge which raises from the garment to provide a highly effective raised barrier.

In accordance with another aspect of the present invention, a machine for applying ribbon to garment material is provided that includes a conveyor for carrying garment material. The conveyor moves in a direction along a flow path. Ribbon is provided for application to the garment material. A ribbon feeder having a first feeder head moves across the flow path to apply the ribbon to the material on the conveyor in a curved contour.

In another aspect of the invention, an adhesive applicator is provided which applies adhesive along one edge of the ribbon prior to application of the ribbon to the material in order that the ribbon is fastened to the material along the one ribbon edge. The resulting free edge of the ribbon may then form a raised barrier on the finished garment.

Also in accordance with the present invention, a method is provided for applying ribbon to garment material that includes the steps of providing garment material with opposing edges that represent waist regions of a finished garment, moving the material in one direction along a flow path, providing a source of ribbon, guiding the ribbon directly onto the material in a pattern moving laterally across said material relative to said flow direction such that the ribbon is applied to the material in a curved contour.

BRIEF DESCRIPTION OF THE DRAWINGS

FIG. 3 taken along line 3—3 in FIG. 1, showing an enlarged front view of the ribbon feeder head.

FIG. 4 is a side view of the ribbon feeder head shown in FIG. 3.

FIG. 10 is a top plan view of a machine for applying ribbon to a garment material according to another embodiment of the present invention.

FIG. 20b is an enlarged front view of a ribbon feeder head of the embodiment of FIG. 20a.

FIG. 21 is a perspective view of one possible disposable absorbent garment produced by the machine shown in FIG. 20a.

DESCRIPTION OF PREFERRED EMBODIMENTS OF THE INVENTION

Figure 1:
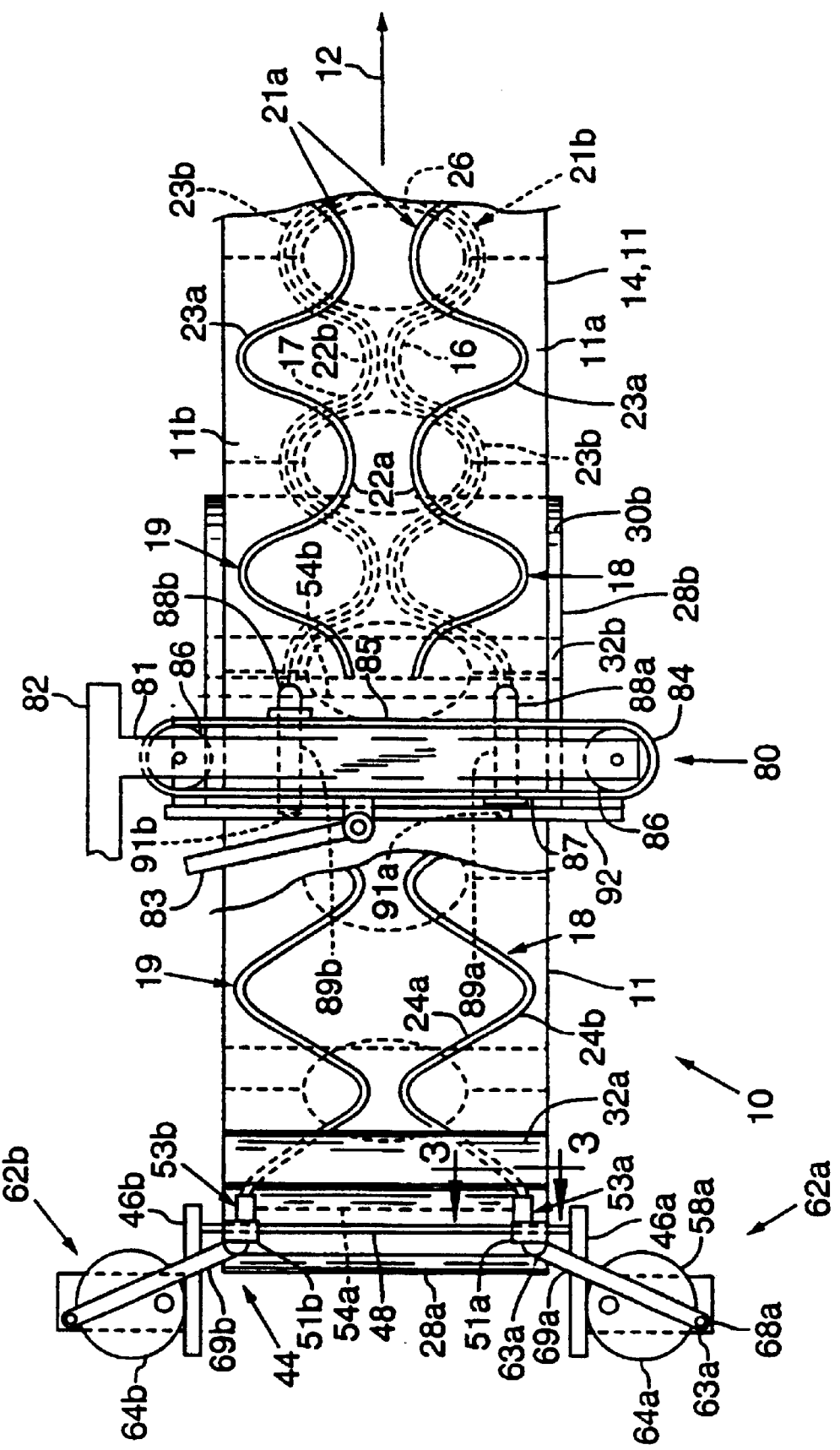
FIG. 1 is a top plan view of a machine for applying ribbon to garment material according to an embodiment of the present invention, with parts of the machine broken away to reveal underlying structure.
Figure 2:
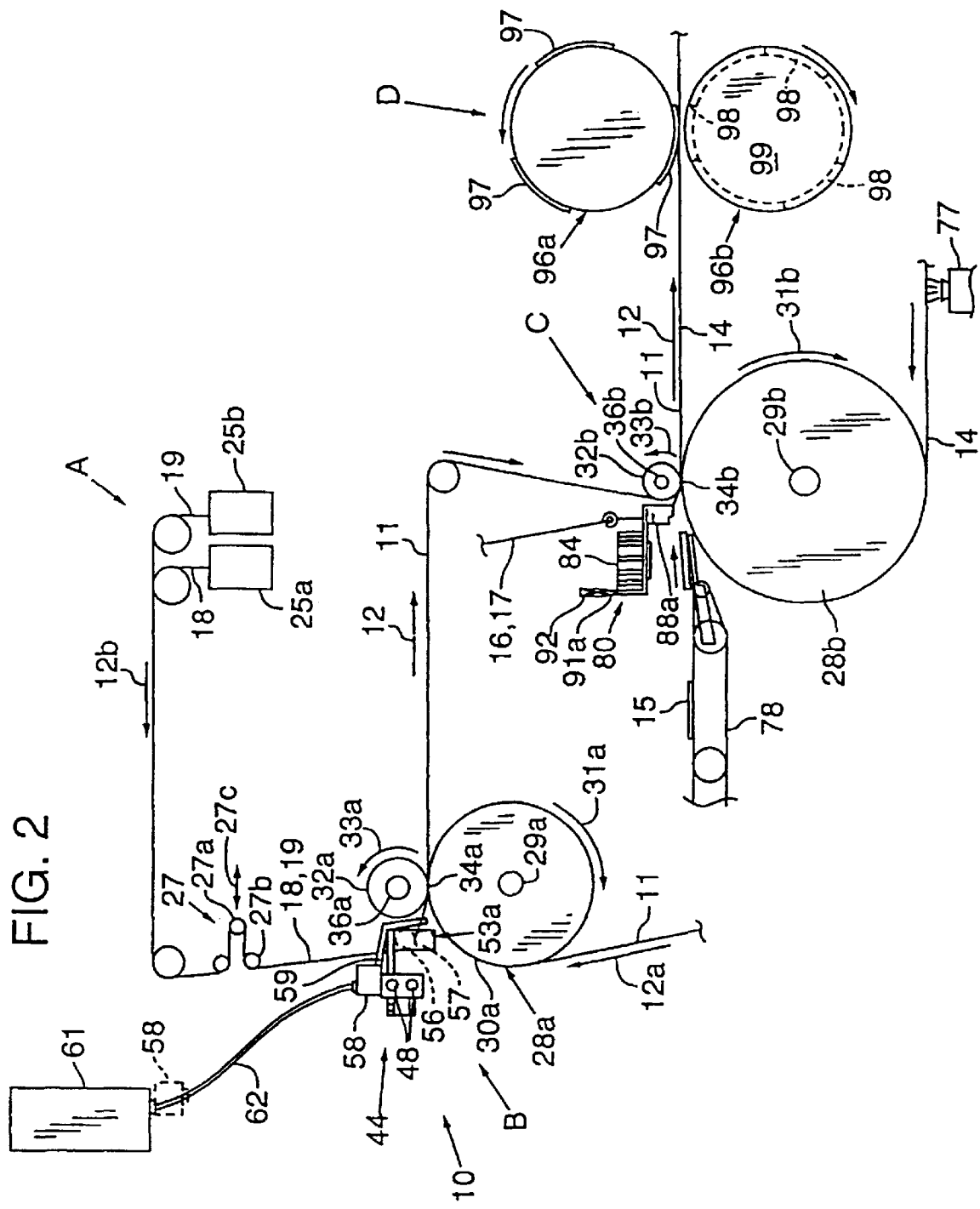
FIG. 2 is a side elevational view of the machine shown in FIG. 1, with additional machine structure shown.

Referring first to FIGS. 1 and 2, a machine, or apparatus, generally indicated at 10 is constructed according to a preferred embodiment of the invention. The machine illustrated is specifically adapted to produce disposable diapers or training pants, but it should be understood that it is not limited to such products.

As is known, disposable diapers and training pants generally include an outer, or backing, sheet of a liquid impervious material, onto which an absorbent pad is placed. A liquid pervious liner, or inner, sheet is placed thereon to encase the absorbent pad therebetween. One garment and method of manufacture is illustrated in U.S. Pat. No. 4,726,807 to Young and Lancaster, which is herein incorporated by reference to illustrate typical materials used and known methods of manufacturing such garments.

Such garments are often continuously manufactured on assembly lines that carry material in a flow, or "machine" direction. For instance, U.S. Pat. No. 5,383,988 to Herrmann and Teodora shows a disposable garment assembly line and is incorporated by reference herein. The garments may be produced in what is referred to as a "cross direction" orientation, wherein both waist regions of the garments are oriented parallel to the flow direction. Garments may also be produced with a "machine direction" orientation, wherein the waist regions extend transversely of the flow direction. In the inventive embodiments described below, a machine is provided which applies ribbon material to form integral inner leg gathers and end caps on disposable absorbent garments which are produced in the "cross direction" orientation. It is to be understood that the present invention may also be applied to "machine direction" garment production.

Figure 5:
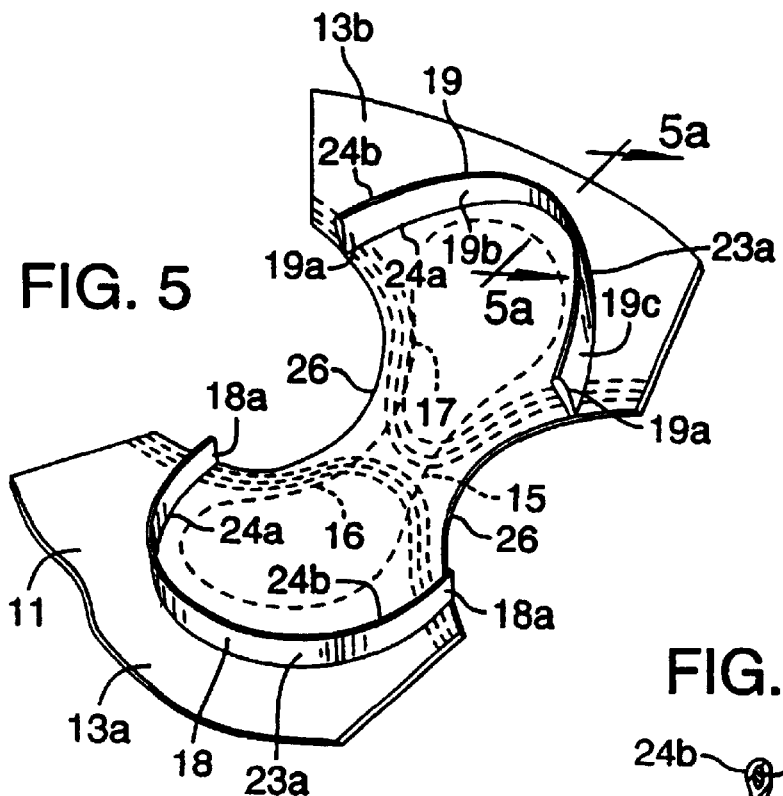
FIG. 5 is a perspective view of a disposable absorbent garment provided by the machine shown in FIG. 1.

Reference is made to FIGS. 1, 2 and 5 for an overview of the garment production machine, and the garment produced thereby. The machine provides a conveyor along which an elongate sheet, or web, of liner material 11 having a selected width is moved in one direction along a flow path 12 which extends in the machine direction. The opposing edges of the material 11a, 11b (FIG. 1) correspond to and will become part of the rear and front waist regions 13a, 13b in the finished garment (FIG. 5). The liner material 11 is laid over a backsheet of backing material 14, with an absorbent pad 15 and a plurality of elastic bands 16, 17 ("leg elastics") encased between the liner and backing materials (see FIG. 2).

First and second ribbons 18, 19 are applied generally longitudinally along the flow path 12 to the outer face of the liner material 11 that faces away from the backing material 14 and the encased leg elastics 16, 17 in the finished garment. The ribbons are applied in a pair of generally symmetric sinuous contours. The sinuous contour of the first ribbon 18 can be of lesser amplitude than the sinuous contours of the second ribbon 19. Both sinuous contours have identical periods and are applied 180° out of phase and combine to produce a curved ribbon contour generally resembling a lop-sided repeating hour-glass contour 21a, with narrow inboard regions 22a and wide outboard regions 23a.

Figure 5A:
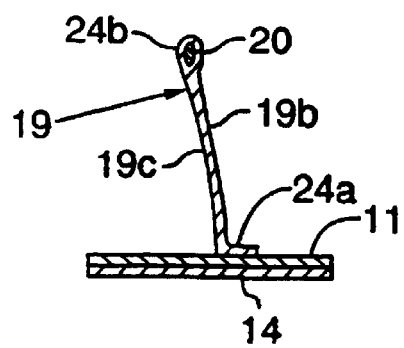
FIG. 5a is a view taken along line 5a—5a in FIG. 5, showing an enlarged view of a barrier flap formed by one preferred type of ribbon.

As shown in FIG. 5a, each ribbon is adhered to the liner material along one edge 24a of the respective ribbon, forming a free edge 24b of the ribbon that will tend to rise from the liner material 11 to form a raised barrier flap on the finished garment. An elongate elastic member 20 may be secured to or encased along the free edge 24b of the ribbon. The elastic member adds tension to the free edge of the ribbon to promote the raising of the ribbon barriers 18, 19 on the garment.

The elastic band member 20 may be adhered to the free edge 24b of the ribbon, or the ribbon may be of folded construction, with the folded edge of the ribbon forming the ribbon free edge 24b and holding the band member 20 therein.

Referring again to FIGS. 1 and 5, the first and second sets of elongate elastic elements 16, 17 (encased between the liner and backing materials) may each include three individual elastic bands. Each of the first and second sets of bands 16, 17 are arranged in a repeating sinuous contour, which together form another generally hour-glass-shaped contour 21b, with narrow inboard regions 22b and wide outboard regions 23b. The ribbon contour 21a applied on the outer face of the liner material 11 is longitudinally offset from the elastic contour 21b such that the wide outboard regions 23a of the ribbon contour 21a are aligned transversely of the flow path with the narrow inboard regions 22b of the elastic contour 21b.

In FIG. 1, oval dashed lines 26 positioned along the center region of the backing and liner sheets 14, 11 indicate leg contour cut-out lines at which material will be severed from the garment in the manufacturing process to form leg openings 26 (FIG. 5). As shown in FIGS. 1 and 5, the inboard regions 22a of the first and second ribbons are cut away from the garment along with the severed material within oval cut-outs 26 such that the outboard regions 23a form arch-shaped standing ribbon barriers extending adjacent the front and rear waist regions of the garment.

The machine thus is capable of producing a disposable absorbent garment with the ribbons 18, 19 providing raised flap-like moisture and particulate barriers in the form of a pair of integral inner leg gathers and end caps. The flap-like ribbon barriers 18, 19 extend in opposing arched curves about each end of the pad 15 in the interior region of the garment, to define a partial oval-shaped exudate containment region in the crotch area of the garment (FIG. 5).

Due to the greater amplitude of the second ribbon 19 sinuous contour relative to the amplitude of the first ribbon 18 contour, the distance between the outboard (i.e., end cap) region 23a formed by the second ribbon 19 and the front waist region 13b is less than the distance between the first ribbon 18 outboard region and the rear waist region 13a. In other words, the forward ribbon barrier 19 extends higher toward the garment waist region than does the rear ribbon barrier 18.

The elastic bands 16, 17 are not cut away with the severed leg opening material. The elastic outboard regions 23b curve around each leg opening 26 and the elastic inboard regions 22b extend across the crotch area between the leg openings 26 to form elastic leg gathers in the finished garment.

The flap-like ribbon barrier 18, 19 construction, in combination with the elastic leg gathers formed by the elastic bands 16, 17 is highly effective at confining bodily waste during and after exudation. As will be described, the dimensions of the leg openings 36 and the shape of the curved ribbon contour 21a may be varied to position the intersection of the ribbon barrier ends 18a, 19a with the leg openings 26, as desired.

Referring to the garment materials, the liquid impervious back sheet 14 may be of a thin thermoplastic material, such as a pigmented polyethylene film having a thickness in the range of 0.02–0.04 mm. The liquid pervious liner sheet 11 may be a carded polyester fiber with a latex binder or a spun-bonded polypropylene having continuous fibers and thermally bonded by patterned calendar rolls. The liner sheet may be impregnated with a surfactant to render it hydrophilic. The absorbent pad 15 may be of wood fibers or other fibers, such as chemical wood pulp, or any other suitable moisture absorbing material such as commercially available fluff pulp or a fluffed bleached craft soft wood pump.

The first and second ribbons 18, 19 are preferably made of non-woven material, such as high-strength spun-bound polypropylene. The non-woven is substantially inelastic, being about 3–5% stretchable. The inner side of the ribbon facing the garment crotch (i.e., side 19b in FIGS. 5 and 5a) may be treated with a surfactant to render it more hydrophilic than the outer side 19c of the ribbon 19 facing the garment waist area. The capillary action of the surfactant-treated inner side 19b of the ribbon will quickly absorb liquid exudates and will tend to hold the exudates by capillary action, preventing their transfer to the outer side 19c of the ribbon and to the areas of the garment outside of the ribbon barriers 18, 19.

Somewhat similarly, a polyethylene film/nonwoven composite material (i.e., like that used for the backsheet material) may be used as ribbon material, with the non-woven side facing the garment crotch area. Such composite material is water-repellent on the polyethylene film side, and soft to the touch on the nonwoven side. The ribbons may have a width of about one inch. It is contemplated that ribbon of other constructions, elasticity and widths may work equally as well.

The elastic material may be 0.015 inch by 0.027 inch, six-strand natural rubber obtained from Fulflex, which has been split into the two sets of three elastic bands 16, 17. Alternatively, eight-strand natural rubber may be split into two sets of four bands. More or fewer elastic bands around the leg openings will also work well under the present invention.

Machine Embodiment No. 1

Describing the machine 10, and referring to FIGS. 1 and 2, the machine has a ribbon supply portion A, a ribbon applicator portion B, a pad and elastic feeder portion C, and a die cutter portion D.

The ribbon supply portion A has a pair of ribbon supply containers 25a, 25b that hold respective supplies of ribbon 18, 19. The ribbon supply portion A may also include a tensioning device 27 with tensioning rollers 27a, 27b.

The ribbon applicator portion B has a first circular conveyer drum 28a that is supported on and driven about a central axle 29a in direction 31a. A first nip roller 32a is mounted above the conveyor drum 28a for rotation in direction 33a about an axle 36a that is substantially parallel to axle 29a.

As shown in FIGS. 1–2, ribbon applicator portion B has a ribbon feeder 44 positioned above the first conveyor drum 28a. A pair of elongate rods 48 extend between frame portions 46a, 46b transversely of the machine flow path 12 and across the first drum face 30a.

First and second ribbon feeder heads 53a, 53b are slidably mounted on rods 48. As shown in FIG. 1, the feeder heads 53a, 53b have slider block portions 51a, 51b, each having a pair of circular bores 50 defined therethrough. As best shown in FIG. 4, the block bores 50 receive the pair of rods 48 for smooth reciprocative sliding action thereon. Referring to FIG. 1, the rods 48 define a linear path 54a for the feeder heads 53a, 53b that extends transversely of the flow path 12.

Further features of feeder head 53a are shown in FIGS. 3 and 4 (feeder block 53b is of mirror-image construction). An inverted U-shaped bracket 55 is mounted to a front surface of slider block 51a. The bracket has elongated top plate 55b that mounts at one end to the slider block. The top plate has an elongate slot 55c defined therein through which a ribbon may extend. The space opposed legs 55a of the bracket extend downwardly from opposite ends of the top plate and may be spaced from the slider block 51a. A pair of contacting rollers 56, 57 are mounted within the legs 55a of the bracket 55 for rotation on parallel horizontal axles 56a, 57a.

An adhesive applicator 58 containing a light-weight pump device may be mounted on the slider block 51a. An elongate pressure tube 59 extends downwardly from the applicator 58 along the inboard leg 55a of the bracket 55. The free end 59a of the tube is directed upwardly. An upwardly oriented adhesive spray head 60 is fixed to the free end of the tube. It is also contemplated that the adhesive applicator may be mounted on the slider block directly behind the bracket 55, in order to permit use of a smaller slider block.

As shown in FIG. 2, a fixedly mounted adhesive reservoir 61 is connected to the adhesive applicator 58 through a flexible tube 62. As shown in the dashed-line depiction of the adhesive applicator 58, the applicator pump may also be remotely mounted adjacent the adhesive reservoir 61. In this case, the tube 62 is a flexible pressure tube that extends from the remote applicator 58 to a connection with pressure tube 59 on the feeder block 51a. Such remote placement of the adhesive applicator minimizes the weight borne by the reciprocating feeder block 51a.

As best shown in FIG. 1, opposing cam devices 62a, 62b are drivingly connected to the respective feeder heads 53a, 53b. The cam devices 62a, 62b have essentially mirror-image construction, and only cam device 62a is described in detail. Cam device 62a includes a cam mounting plate 63a that extends from the frame 46a and supports a horizontally rotating cam 64a. A contact roller 68a is spring-biased to ride against the periphery of cam 64a as the cam rotates. A connecting rod 69a extends from the contact roller 68a to a pivot attachment 63a on the feeder head 53a.

The elastic applicator portion C will now be described. As best shown in FIG. 2, a second nip 34b is formed between a second conveyer drum 28b, and a second nip roller 32b. The second drum 28b is supported on a central axle 29b and rotates in direction 31b. The second nip roller 32b is mounted above the second conveyor drum 28b for rotation in direction 33b about an axle 36b that is substantially parallel to drum axle 29b.

An adhesive applicator 77 for applying adhesive to the backing material 14 is positioned beneath the second conveyor drum 26b.

An absorbent pad conveyor 78 is positioned adjacent the second nip 34b above the second drum 28b.

Figure 5B:
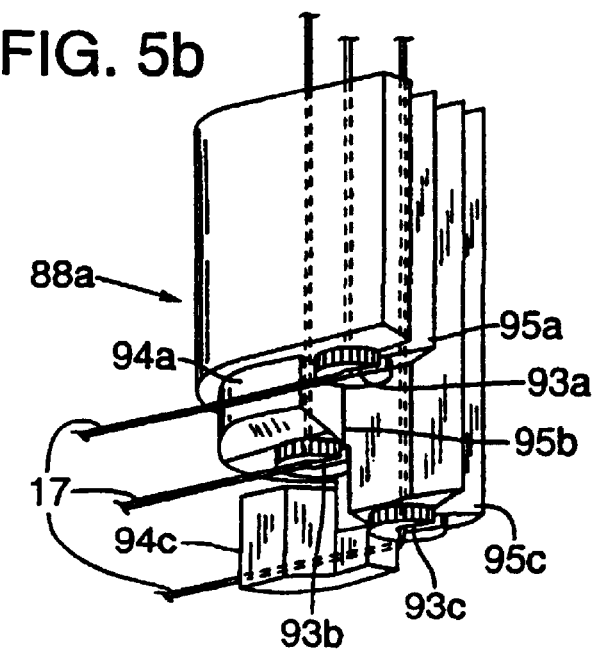
FIG. 5b is an enlarged perspective view of an elastic band feeder head shown in FIG. 2.

An elastic band applicator 80 is positioned adjacent the second nip 34b above the absorbent pad conveyor 78. The elastic band applicator maybe constructed and function as illustrated in FIGS. 1, 2 and 5b, and which is described in a U.S. patent application Ser. No. 08/493,425 of Thomas R. Herrmann, filed on Jun. 22, 1995, incorporated herein by reference.

The elastic applicator 80 applies the two sets of three individual elastic bands 16, 17 onto the backing sheet 14 at the second nip 34b.

As shown in FIGS. 1 and 2, an elongate support member 81 extends from a frame member 82 transversely above and across the second drum face 30b and flow path 12. A reciprocating belt 84 is trained about a pair of pulleys 86 which are rotatably mounted on the support member 81. The trained belt thus has opposing front and rear linear portions 85, 87, respectively, extending transversely across the flow path 12. A cam-driven connecting arm 83 is attached to the rear linear belt portion 87.

Elastic feeder heads 88a, 88b are respectively attached to brackets 89a, 89b, which are mounted on front and rear linear belt portions 85, 87, respectively. The brackets 89a, 89b have rear flanges 91a, 91b slidably mounted within a grooved guide member 92 that extends transversely across the flow path 12.

As shown in FIG. 5b, the elastic feeder head 88a is configured with first, second and third vertical guide slots 95a, 95b, 95c defined in the back of the feeder head. The guide slots respectively open at bottom portions thereof onto a first peripheral elastic band guide platform 93a adjacent a first arcuate peripheral guide surface 94a, a second central elastic band guide platform 93b, and a third peripheral elastic band guide platform 93c adjacent a second arcuate peripheral guide surface 94c. The arcuate guide surfaces have center axes of curvature which are vertically oriented and located at the central guide opening 93b.

Die cutter portion D will now be described. The die cutter may include a pair of counter-rotating upper and lower drums 96a, 96b. The periphery of the upper drum 96a may be configured with one or more protruding die cutter blades 97, which closely mate with the walls of like-shaped die apertures 98 on the lower drum. The lower drum 96b has a hollow interior 99.

Machine Operation

As illustrated in FIGS. 1 and 2, garment liner material 11 is moved in one direction along the flow path 12. As the first conveyer drum 28a rotates in the direction indicated by arrow 31a, the peripheral face 30a of the first drum supports liner material 11 as it travels in direction 12a from the side to the top of the drum 28a. The drum is wider than the usual width of material to be carried thereon so that it can accommodate sheet material of different widths.

At the ribbon supply portion A, elongate strips of ribbon 18, 19 are drawn from respective ribbon supply containers 25a, 25b and are carried in the direction of arrow 12b. The first and second ribbons 18, 19 are guided from first and second positions on feeder heads 53a, 53b which reciprocate transversely across the liner material relative to the flow path direction and adjacent the first nip 34a under the direction of rods 40 operated by cams 64a, 64b.

As shown in FIG. 2, it may be desirable to maintain a substantially constant tension in the ribbons while feeding the ribbons from the feeder heads to the first nip 34a. To provide for such constant tension, the ribbons may be threaded through the tensioning device 27 provided upstream of the feeder heads 53a, 53b. Such a tensioning device 27 varies the tension in the ribbons feeding into the feeder heads in order to counteract the variance in tension generated by the acceleration of the feeder heads along the linear path in applying the curved ribbon contours. The ribbon is threaded through the plurality of rollers 27a, 27b of the illustrated tensioning device 27. At least one of the rollers 27a is linearly movable (as indicated by arrow 27c) to vary the tension in the ribbon.

The ribbons 18, 19 are respectively guided through feeder heads 53a, 53b that reciprocatively ride on the rods 48. Applying the ribbons 18, 19 from the reciprocating feeder heads directly to the moving sheet of liner material 11 at the first nip 34a produces the curved "hour glass" contour 21a. First nip roller 32a counter-rotates relative to the conveyor drum in the direction indicated by arrow 33a and tightly presses the ribbons 18, 19 onto the liner material 11 carried by the first conveyer drum 28a at the first nip.

Tube 62 feeds adhesive from the adhesive reservoir 61 to the adhesive applicator 58 while the applicator 58 moves with the reciprocating feeder heads 53a, 53b. The adhesive applicator 58 applies adhesive to the ribbon after the ribbons are fed through the feeder heads 53a, 53b, and before the ribbons reach the first nip 34a. The ribbons 18, 19 are fed from above through the slot 55c in the bracket top plate 55b. From the slot, the ribbon is fed between the counter-rotating rollers 56, 57 (counter-rotating in respective directions 56b, 57b) for application to the liner material 11 at the first nip 34a.

As shown in FIG. 3, the adhesive applicator head 60 is positioned on the upwardly directed pressure tube end 59a beneath the inboard edge 24a of the emerging ribbon 18, just downstream of the counter-rotating rollers 56, 57. The adhesive spray head 60 directs a narrow spray of adhesive onto the ribbon adjacent the inboard edge 24a of the ribbon 18. As the ribbons are fed to the first nip 34a, the sprays form continuous strips of adhesive along the inboard edges of ribbons 18, 19 to firmly fasten the ribbons to the liner sheet 11.

The outboard "free" edge 24b of the ribbon will be somewhat tensioned during application to the liner sheet, due to the free edge being on the outer periphery of the outboard portion 23a of the curved ribbon contour. The free edge of the ribbon thus tends to stand up from the liner sheet to form a raised barrier (see FIG. 5a). Provision of the elastic member 20 in the free edge of the ribbon will further promote the standing of the free edge.

To prevent the ribbon from lateral drifting between the counter-rotating rollers 56, 57, the rollers have an axial dimension just greater than the width of the ribbons 18, 19, and the opposed ends of rollers 56, 57 are closely spaced within the legs 55a of the bracket 55.

The feeder heads 53a, 53b are positioned in close proximity to the first nip 34a to precisely apply the ribbons onto the material 11. The feeder heads 53a, 53b are driven by the cam mechanisms 62a, 62b. The spring-biased contact roller 68a rides against the cam 64a as the cam rotates. A single belt and pulley or other drive mechanism may drive both cams 64a, 64b in order to maintain the proper phase relationship between the rotation of the cams.

When the cams 64a, 64b rotate, the first and second feeder heads 53a, 53b are driven in opposing reciprocative directions along the linear path 54a to form the hourglass-shaped ribbon contour 21a. Since the contour of ribbon 19 is "deeper" than the contour of ribbon 18, cam 64b has a diameter greater than that of cam 64a to reciprocate feeder head 53b through a longer stroke.

The sinuous shape of the curved ribbon contour 21a may be modified by varying the shape of the cams 64a, 64b. Thus, any of a variety of sinuous ribbon curves that are effective in managing exudates may be produced through application of the cam mechanism. For illustrative purposes, cams 64a, 64b are shown with a simple circular shape, which produces a simple curved contour. However, the cam shapes may be varied to produce different ribbon curves.

As will be appreciated by attention to FIGS. 1 and 2, the shape of the ribbon contour 21a is related to the ratio of the rate of lateral motion of the feeder heads across the flow path 12 (feeder rate) and the rate of motion of the first conveyor drum face 30a in the flow path direction 12 (conveyor rate). In general, the ribbons are applied at a maximum angle relative to the flow path 12 when the feeder rate is at its maximum speed. Conversely, the ribbons are applied parallel with the flow path when the feeder rate is zero, meaning the feeder heads 53a, 53b are stationary along the linear path 54a. Mathematically expressed, the ribbons 18, 19 extend relative to the flow path 12 at an angle=arctan (feeder rate÷conveyor rate).

Once the ribbons 18, 19 are applied to the upper surface of the liner material 11, as shown in FIGS. 1 and 2, the liner material is conveyed downstream to the elastic applicator portion C, where the elongate elastic bands 16, 17 are encased between the liner material 11 and the backing material 14 at the second nip 34b.

The adhesive applicator 77 applies adhesive to the side of the backing material sheet 14 that receives the elastic. The adhesive applicator 77 sprays adhesive onto the backing material upstream of the second conveyor drum 28b to prevent accumulation of any possible overspray on the conveyor drum 28b. The adhesive may be applied over the entire outward width of the backing material sheet 14 to provide adhesion for the sets of bands 16, 17, pads 15 and overlying liner sheet 11.

At the second nip 34b, the peripheral face 30b of the second conveyer drum supports backing material 14 as it travels from the bottom to the top side of the drum in FIG. 2. The second drum 28b is driven in a direction indicated by arrow 31b. The second nip roller 32b counter-rotates relative to the conveyor drum in the direction indicated by arrow 33b and presses against drum 28b at the second nip 34b. The nip of the second nip roller 32b and second conveyor drum 28b tightly presses the backing material 14 and the liner material 11 over the sets of bands 16, 17.

The absorbent pad conveyor 78 is operable to carry the longitudinally spaced pads 15 and insert them at the second nip 34b such that pads are captured between the backing and liner sheets 14, 11.

Referring now to the reciprocating belt 84, the front and rear linear portions 85, 87 of the belt move in opposite directions when the belt is moved. The mounting of the brackets 89a, 89b respectively on the front and rear linear belt portions 85, 87 thus yields simultaneous, symmetric, reciprocative movement of both elastic feeder heads 88a, 88b along a linear path 54b extending transversely of the flow path when the belt is reciprocated by the connecting rod 83.

The sets of elastic bands 16, 17 are guided from above through the respective reciprocating feeder heads 88a, 88b directly onto the backing material 14 at the second nip 34b. The elastic bands 16 are guided through the slotted elastic band openings 95a, 95b, 95c. The outermost of the bands 16 are guided from peripheral guide openings 93a, 93c and along respective arcuate guide surfaces 94a, 94b. The outermost bands 16 extend tangentially from the arcuate guide surfaces 94a, 94c to the second nip 34b. The center band 16 is guided from the central opening 93b. The three bands 16 are thus guided from the feeder head 88a with a constant spacing maintained between the bands.

As shown in FIG. 1, reciprocation of the feeder heads 88a, 88b applies the elastic bands in another sinuous curved "hour glass" contour with its wide outboard portion 23b aligned transversely of the flow path with the narrow inboard region 22a of the ribbon curved contour 21a.

The elastic feeder heads 88a, 88b are positioned as close as possible to the second nip 34b to precisely apply the bands 16, 17 onto the materials 14, 11 at the second np 34b.

It is to be understood that elastic feeder heads of various constructions, including those that apply elastic bands without a constant spacing between individual elastic bands, may be used with the present invention. Furthermore, the elastic feeder heads 88a, 88b may be rod-mounted as described above relative to the ribbon feeder heads 53a, 53b. It is also contemplated that ribbon feeder heads 53a, 53b may be belt-mounted as described in relation to the elastic feeder heads 88a, 88b.

The combined backing and liner sheet with an absorbent pad encased therebetween are carried downstream, to the right in FIGS. 1 and 2, to the die cutter portion D which cuts away the material for the garment leg openings 26 in the oval area defined by dashed lines 26 in FIG. 1. The close mating of the cutter blades 97 of the upper drum 96a with the walls of the die apertures 98 of the lower drum 96b cuts away the leg opening material, along with the inboard portion 22a of the applied ribbons in order to form the front and rear flap-like ribbon barriers 18, 19 on the garment. The leg opening material falls into the interior 99 of the lower drum as waste, and may be removed by a vacuum or the like. It is also contemplated that the cutting-away of the leg opening material may be accomplished with known high-pressure water knives or other appropriate means. The shape of the ribbon contour, the amount of ribbon overlap and the leg opening dimensions are selected to establish the positions of the intersections of the ribbon barrier ends 18a, 19a with the leg openings 26 in the finished garment.

Alternative Ribbon Feeder Head

Figure 6:
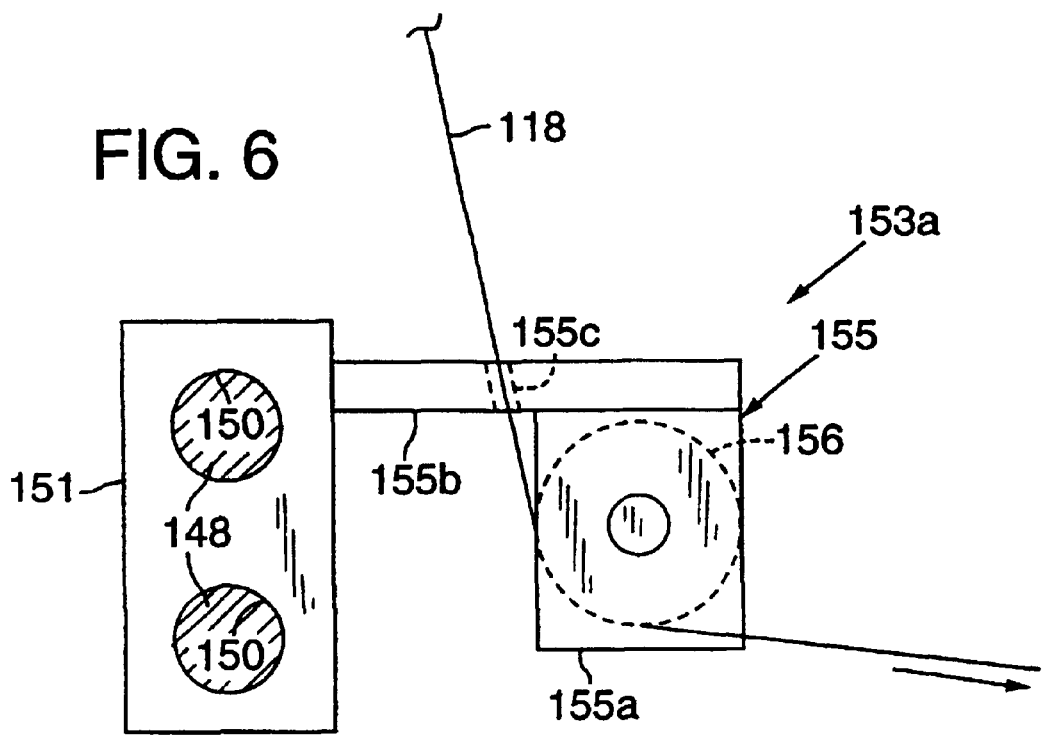
FIG. 6 is a side elevational view of a ribbon feeder head of another embodiment of the present invention.

An alternative ribbon feeder head 153a is shown in FIG. 6. The ribbon feeder head 153a is similar to the feeder head 53a described above, with similar structures indicated with corresponding "100" series numbers. The ribbon feeder head 153a has a single roller 156 under which the ribbon 118 is guided. The ribbon approaches the feeder head from above, is guided through a slot 155c in the top plate 155b of the inverted U-shaped bracket 155, and is guided along the side and bottom of the roller to the nip. The single roller is held closely within the legs of the bracket 155 and is sized just larger than the width of the ribbon 118 to prevent the ribbon from drifting on the roller 156.

The single roller structure of feeder head 153a permits the application of glue to the ribbon 118 prior to the feeding of the ribbon through the feeder head. The glue is sprayed onto the inboard edge of the lower surface of the ribbon and thus will not contact the roller 156. An adhesive applicator may accordingly be mounted adjacent the ribbon upstream of the feeder head to apply adhesive along the edge of the ribbon.

It should also be understood that the particular ribbon feeder heads described herein are exemplary only, and that other ribbon feeder head embodiments may work equally as well under the invention. For instance, feeder heads with ribbon-guiding slots or grooves defined by stationary guide surfaces may work as well as the roller-configured feeder heads described above.

Machine Embodiment No. 2

Figure 7:
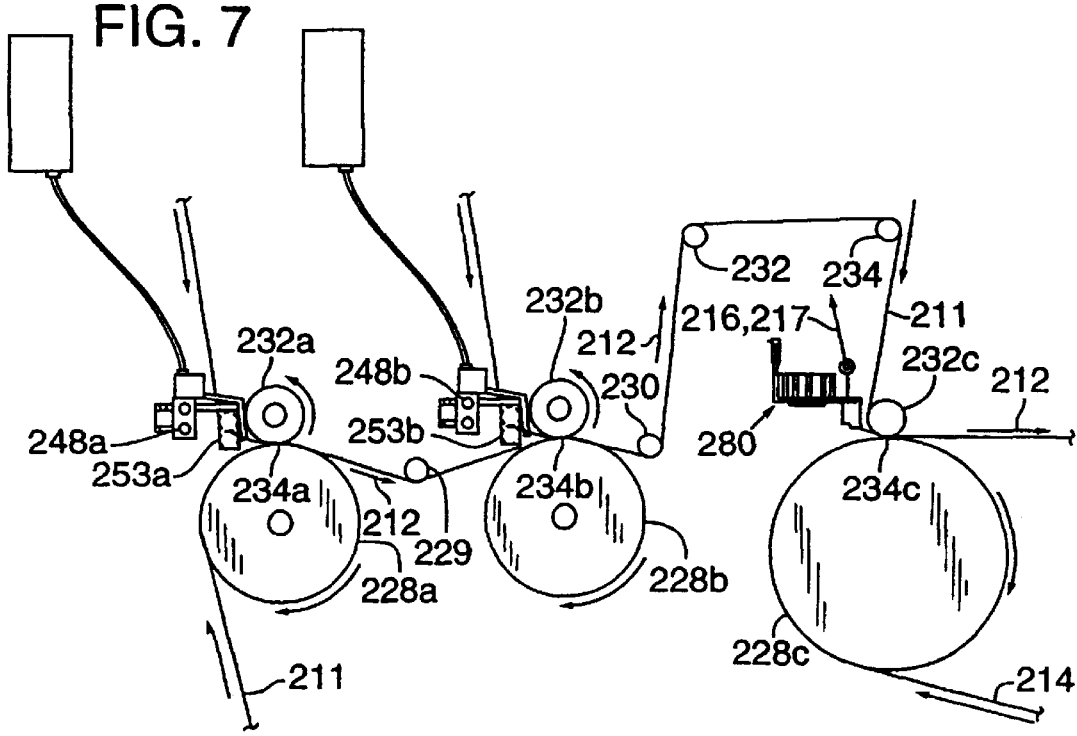
FIG. 7 is a side elevational view of a machine for applying ribbon to material according to another embodiment of the present invention.
Figure 8:
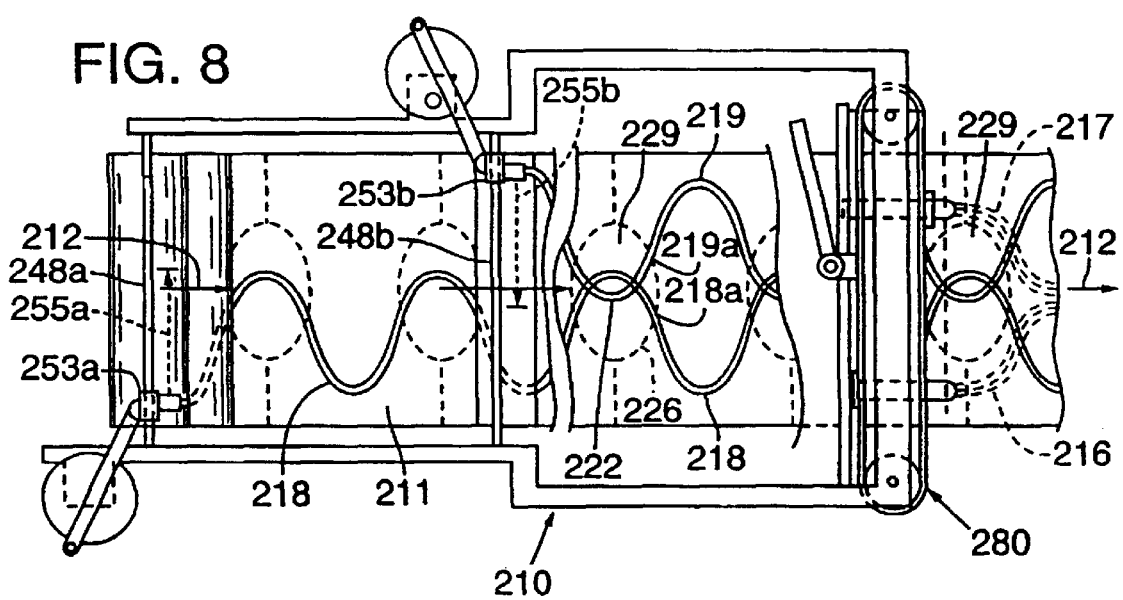
FIG. 8 is a top plan view of the machine shown in FIG. 7, with portions broken away to reveal underlying structure.

FIGS. 7 and 8 show another embodiment of the present invention with reference numerals in the "200" series. In this embodiment, ribbon feeder heads 253a and 253b are staggered along the flow path 212. The staggered feeder heads apply the ribbons 218, 219 in curved contours that overlap in the leg opening areas 226 of the garment at the center of the flow path 212.

As is best shown in FIG. 7, two separate ribbon application nips 234a, 234b are established by counter-rotating first and second pairs of conveyor drum and nip rollers 228a, 232a and 228b, 232b. A bias roller 229 may be positioned between the first and second nips 234a, 234b to urge the liner material 211 upon the conveyer drums 228a, 228b. The feeder heads 253a, 253b are reciprocatively mounted on separate pairs of transversely mounted rods 248a, 248b respectively extending adjacent the first and second nips 234a, 234b.

As indicated in FIG. 8, the feeder heads 253a, 253b are reciprocated through respective strokes 255a, 255b that cross the center of the flow path 212 in order to produce the overlapped ribbon portions 222 at the center of the flow path. The overlapped portions are cut away with the material of the leg openings 226 from the finished garment.

As shown in FIG. 7, the liner material 211 with the overlapping ribbons 218, 219 applied thereon is then conveyed, i.e, by rollers 230, 232, 234, from above to a third nip 234c formed between a third nip roller 232c and a third conveyor drum 228c. Leg elastic bands 216, 217 are applied by the elastic feeder 280 for encasement between the backing and liner materials 214, 211 at the third nip 234c, in the manner described above.

As shown in FIG. 8, the overlapping of the ribbons produces opposing ribbon barriers 218, 219 with closely spaced ends 218a, 219a at the leg openings 226 of the finished garment. Such closely spaced ribbon barrier ends 218a, 219a help improve the sealing capability of the barriers.

Figure 9:
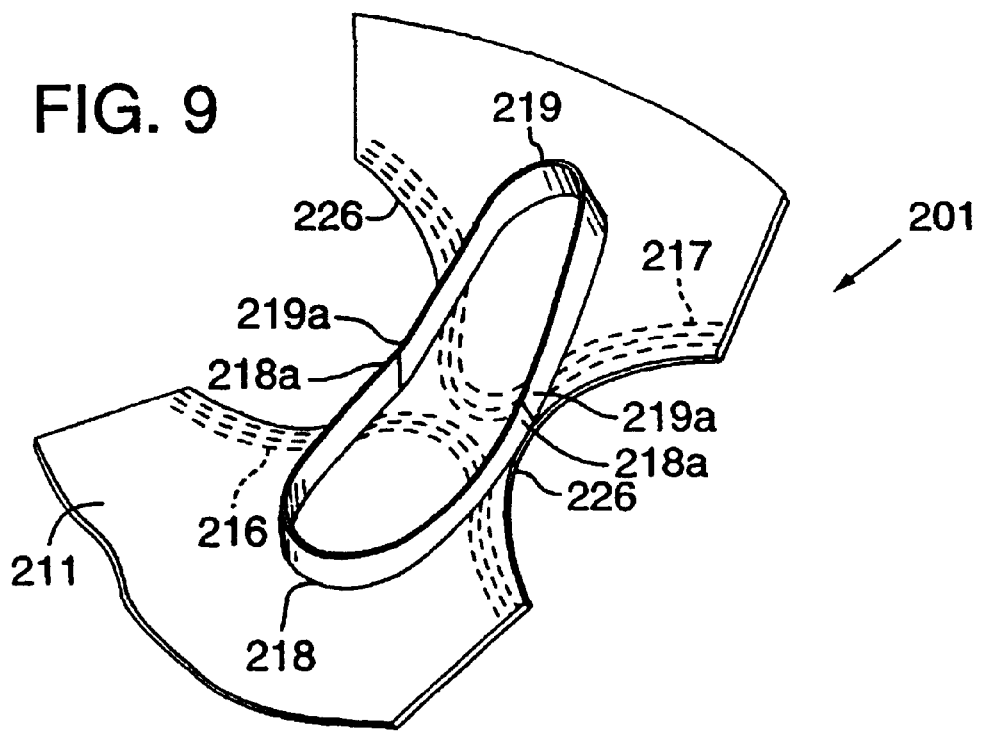
FIG. 9 is a perspective view of one form of disposable absorbent garment which may be produced by the machine shown in FIGS. 7 and 8.

The staggered feeder heads 253a, 253b of FIGS. 7 and 8 may also be reciprocated through a still longer stroke across the center of the flow path 212 in order to produce the garment 201 shown in FIG. 9. In this case, the ribbons 218 and 219 are applied to the liner material 211 so that the ribbons intersect each other adjacent the contour of the leg opening 226. Thus, the ribbon ends 218a, 219a intersect or nearly intersect with each other adjacent the leg openings 226 of the finished garment. Such ribbon barriers 218, 219 thus formed provide a substantially continuous flap-like barrier about the crotch area of the garment.

Machine Embodiment No. 3

FIG. 10 shows another machine embodiment 310a according to the present invention. This embodiment may be used to retrofit an existing garment machine 310b which produces garments with the liner sheet 311 face-down on the conveyer surface, instead of face-up, as in the machine embodiments shown FIGS. 1, 2, 6 and 8. One machine that may be retrofitted is that described in U.S. Pat. No. 5,389,173 to Merkatoris, et al., incorporated by reference herein.

A ribbon-applying machine portion 313 conveys liner material with applied ribbons 318, 319 along a first flow path 315 that is perpendicular to the existing machine flow path 312. In this way, the ribbon-applying portion 313 does not impinge on structure of the existing machine 310. It is also to be understood that the ribbon applying portion 313 may also have other orientations relative to the existing machine, such as a position above the existing machine.

Figure 11:
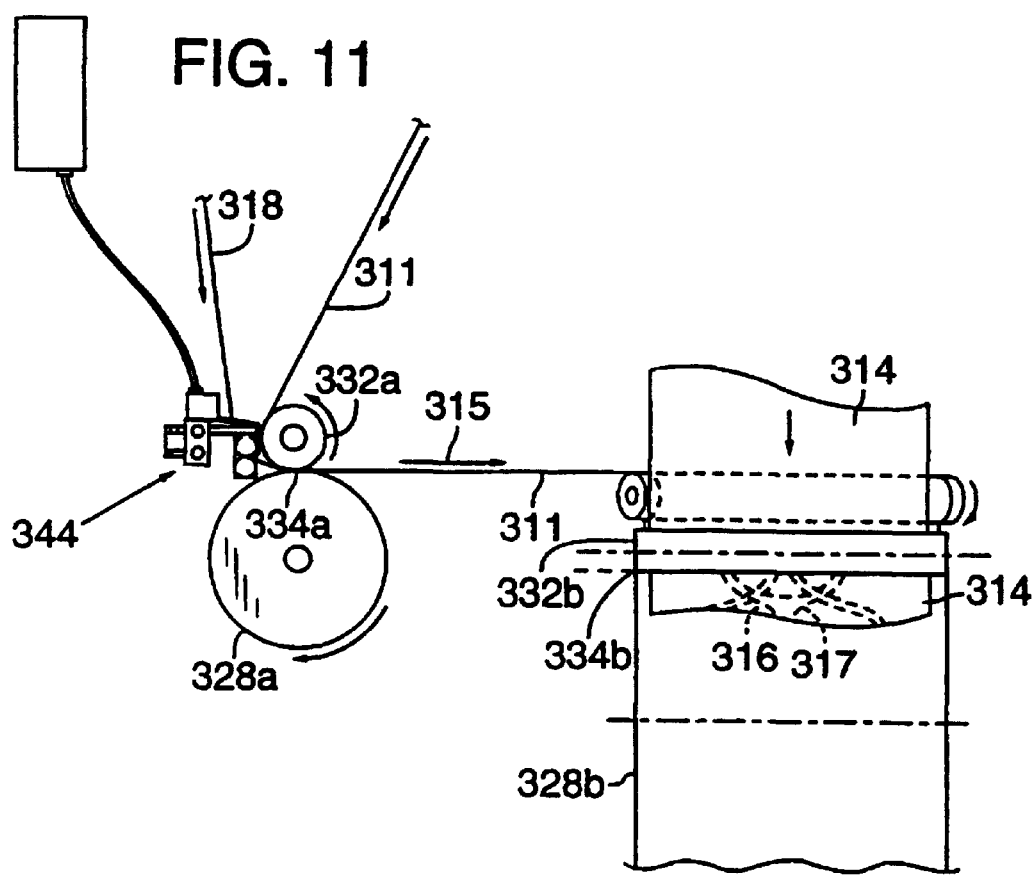
FIG. 11 is an elevational view taken along line 11—11 in FIG. 10.

The ribbon-applying portion has a ribbon applicator 344 and first nip 334a similar to applicator 44 and first nip 34a described in relation to the embodiment of FIGS. 1–4. However, as shown in FIG. 11, the liner material 311 is conveyed from above onto the first nip roller 332a, instead of the first conveyor drum 328a. The ribbons 318, 319 are applied to the bottom face of the liner material 311.

Figure 12:
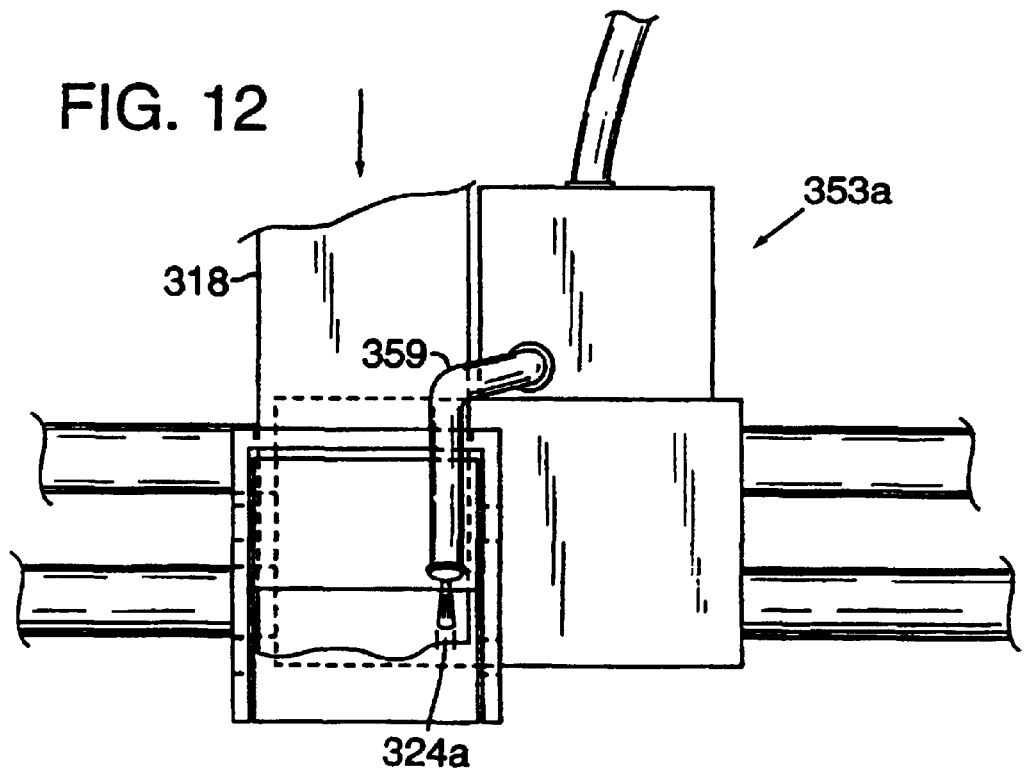
FIG. 12 is an enlarged front view of a ribbon feeder head of the embodiment of FIGS. 10 and 11.

As is shown in FIG. 12, the ribbon feeder head 353a of this embodiment is similar to the feeder head 53a illustrated in FIG. 3. The primary difference is that the pressure tube 359 of feeder head 353a is routed to spray adhesive onto the top of the inboard edge portion 324a of the ribbon 318. In this way, the ribbons 318, 319 are adhered to the bottom surface of the overlying liner material 311 at the first nip 334a.

As shown in FIGS. 10 and 11, the liner material 311 with the downwardly facing applied ribbons then is conveyed along first path 315 toward the existing machine flow path 312. A first redirection roller 330 is positioned for rotation about a horizontal axis 338 that bisects the angle between the first and existing flow paths 315, 312 (i.e., at a 45° angle from both flow paths 315 and 312). The liner material 311 winds from top to bottom about the first redirection roller 330 to flow in direction 340, which is opposite to the direction of the existing flow path 312.

The liner material 311 then winds from top to bottom about a second redirection roller 344. The roller 344 is positioned for rotation about an axis 346 that extends transverse of the existing flow path 312, in order that the liner material 311 is redirected to flow in the direction of the existing flow path 312.

The liner material 311 with the downwardly facing applied ribbons 318, 319 is next conveyed to second nip 334b defined between second nip roller 332b and conveyer drum 328b. As shown in FIG. 11, backing material 314 is conveyed from above around the bottom of second nip roller 332b and through nip 334b, where it is applied on top of the liner material 311.

Leg elastics 316, 317 are encased between the backing material and the liner material at nip 334b. Feeder heads 353a, 353b are slidably mounted for reciprocative movement on a pair of horizontally aligned rods 348. The feeder heads each have a flat guide portion 354a, 354b with three eyelets defined therein to guide the elastic bands 316, 317. The spacing between the bands applied with such feeder heads will vary somewhat as the feeder head speed along the rods varies.

Machine Embodiment No. 4

Figure 13:
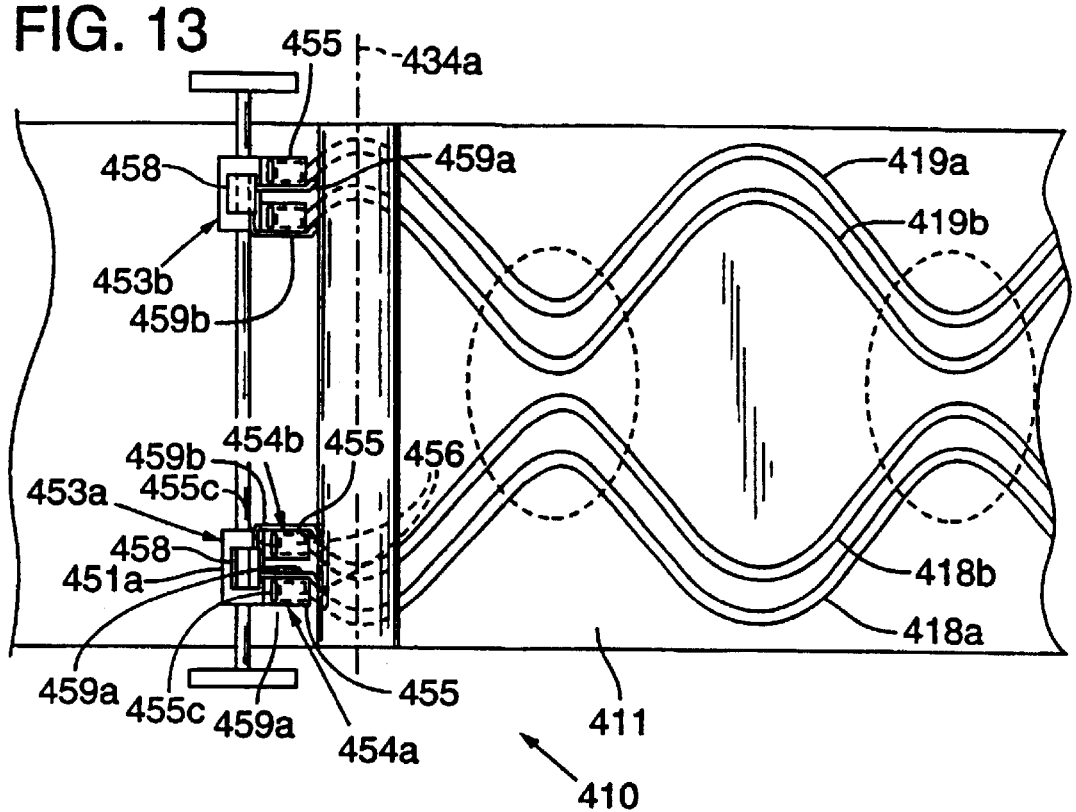
FIG. 13 is a top plan view of a machine for applying ribbon to a garment material according to another embodiment of the present invention.
Figure 14:
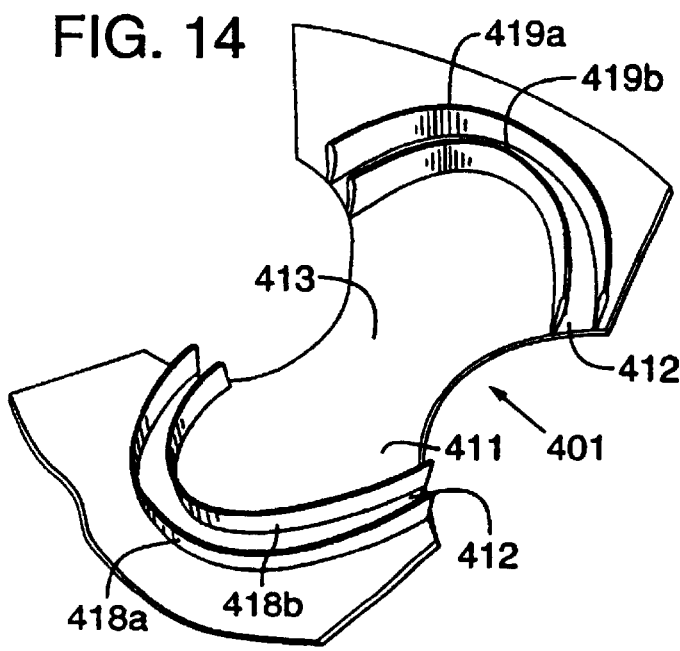
FIG. 14 is a perspective view of one form of disposable absorbent garment which may be produced by the machine shown in FIG. 13.

FIG. 13 shows another machine embodiment 410 of the present invention with reference numerals in the "400" series. In this embodiment, multiple-ribbon feeder heads 453a, 453b each apply a plurality of parallel ribbons to form a multiple "ruffle" ribbon barrier on a garment 401 (FIG. 14). Referring to FIG. 13, multiple ribbon feeder head 453a (and feeder head 453b having mirror-image construction) has a pair of ribbon feeder subheads 454a, 454b mounted on a single rod-mounted slider block 451a. The two subheads 454a, 454b are constructed with a pair of rollers 456 held within an inverted U-shaped brackets 455, much like the feeder heads illustrated in FIGS. 3 and 4. Two ribbons 418a, 418b are guided from above through subhead bracket slots 455c and between the subhead rollers 456 onto the liner material 411 at a nip 434a.

An adhesive applicator 458 may be mounted on the slider block 451a with a pair of pressure tubes 459a, 459b extending therefrom and positioned to spray adhesive along the lower inboard edges of the ribbons 418a, 418b just downstream of the feeder head. The multiple ribbons may be applied from each feeder head in repeating sinuous patterns that are similar to those discussed in the above embodiments.

FIG. 14 shows a garment 401 produced by the machine of FIG. 13. The garment has "ruffled" multiple parallel ribbon barriers 418a, 418b and 419a, 419b disposed in arched curves about the crotch area 413 of the garment. The ruffled ribbon barriers provide redundancy in the exudate containment of the garment, which permits use of relatively thin ribbons to effectively manage exudates. The raised structure of the parallel ruffled ribbons 418a, 418b and 419a, 419b also tends to raise the liner material 412 between the parallel ribbons away from a wearer's skin, providing a comfortable but highly effective exudate barrier. The multiple ribbon feeder heads may also be configured to feed three, four or more ribbons to establish a relatively wide ruffled barrier region on the garment liner material. It is also contemplated that the multiple ribbon feeder heads 453a, 453b may be applied to the staggered feeder head machine embodiment illustrated in FIGS. 7 and 8. Such application would produce a garment with an oval-shaped ruffled barrier area which completely encloses the crotch area of the garment.

Machine Embodiment No. 5

Figure 15:
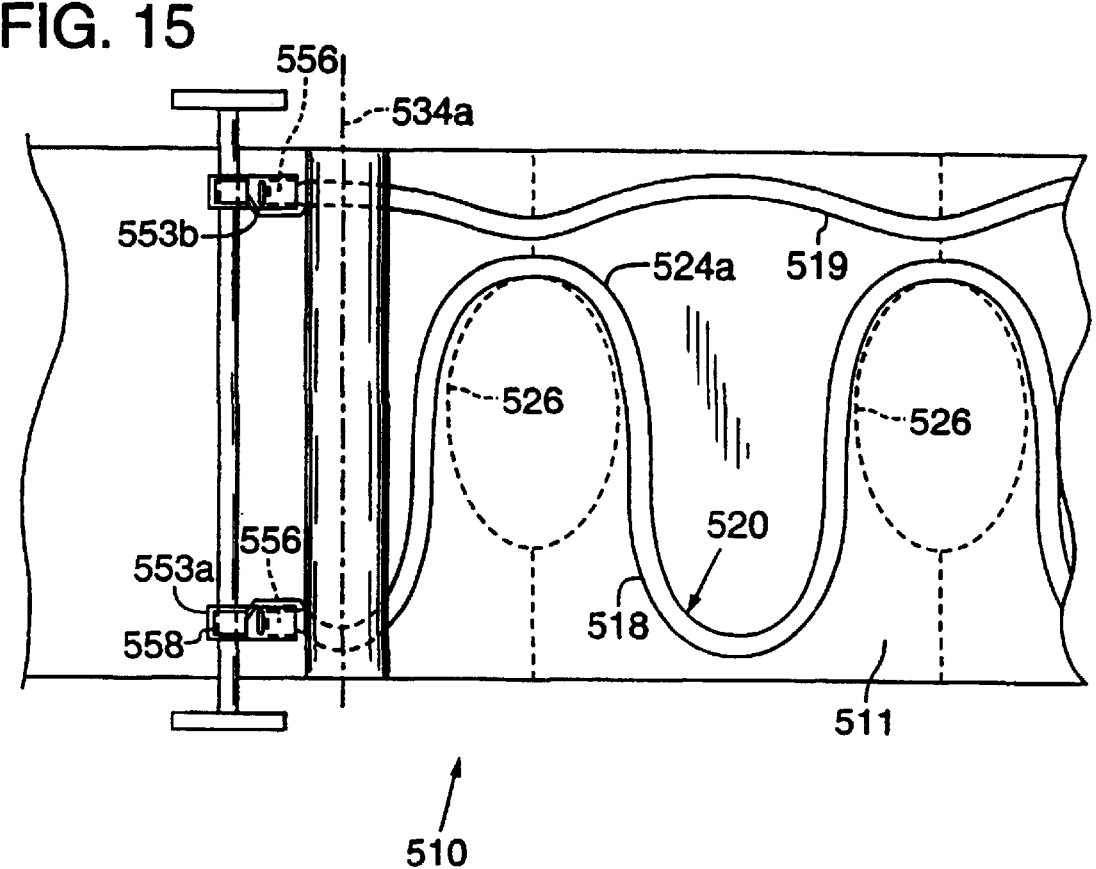
FIG. 15 is a top plan view of a machine for applying ribbon to a garment material according to yet another embodiment of the present invention.

FIG. 15 shows another embodiment of the present invention with reference numerals in the "500" series. The machine 510 produces a garment 501 (FIG. 16) with a deeply contoured "cup" barrier 520 in the crotch and rear of the garment that seals around a wearer's bottom to contain exudates. Referring to FIG. 15, feeder head 553a applies a single ribbon 518 to the liner material 511 at a nip 534a. Feeder head 553a is constructed like feeder head 53a illustrated in FIGS. 3 and 4, except for the adhesive applicator 558 being mounted directly behind the feeder rollers 556 on the feeder head.

Feeder head 553a applies ribbon 518 in a deep sinuous contour to form the "cup" barrier 520. An adhesive applicator 558 as discussed above applies adhesive to the ribbon edge 524a (the top, or inner, edge of ribbon 518 in FIG. 15) so that the ribbon is fastened along edge 524a to the liner material 511. The ribbon 518 curves closely along the forward side of the garment leg openings 526 and extends rearwardly around the crotch region 513a between the leg openings in a tall arched curve that peaks in the central rear portion 513b of the garment adjacent the garment rear waist region 513c.

Figure 16:
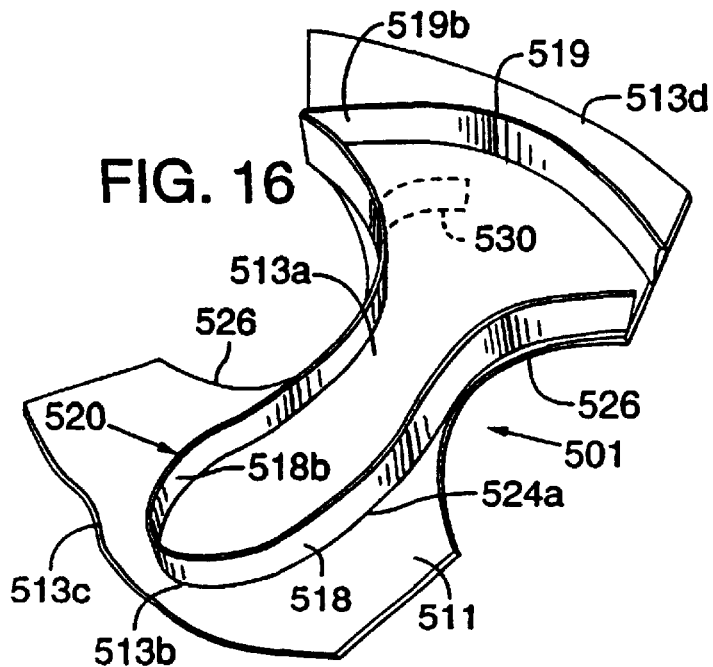
FIG. 16 is a perspective view of one form of disposable absorbent garment which may be produced by the machine shown in FIG. 15.

Referring to FIG. 16, a mild, skin-friendly adhesive may be applied surface 518b of the cup ribbon 518 facing the garment crotch area. The adhesive ribbon surface 518b then may be adhered to a wearer's skin to provide a exudate seal about the wearer's bottom which is highly effective with hard-to-manage exudates such as loose bowel movement exudate. In this case, the garment 501 may be particularly effective as a night-time diaper for infants who are experiencing diarrhea.

To protect the adhesive ribbon surface 518b while the garment is in storage prior to use, the ribbon 518 may be provided with a protective plastic backing tape 530 (dashed outline in FIG. 6) that is pulled away just before the garment is fitted on a wearer. To ensure an effective seal on the wearer's bottom, the ribbon 518 may be as wide as desired.

While the garment 501 offers excellent exudate management with the ribbon cup 520 alone, an additional ribbon seal 519 may be provided along the front of the garment. Such front ribbon 519 may be applied to the liner material by feeder head 553b as shown in FIG. 15. Feeder head 553b applies the ribbon 519 in a relatively shallow sinuous contour generally along the front waist region 513d of the garment. The surface 519b of ribbon 519 facing the garment crotch area may also be provided with adhesive to seal along the front waist region of the wearer. With ribbon 519 and ribbon cup 520 having adhesive seals, the garment 501 forms a substantially continuous and adhesively sealed exudate enclosure on the wearer.

It is also contemplated that the ribbon cup 520 may be formed on the front of the garment. FIG. 16 generally illustrates such a garment if 513b is considered to designate the garment front waist area. Such forward-oriented ribbon cup provides an excellent seal against urine leakage, especially when the adhesive ribbon seal is provided. Such a garment is particularly effective as a night-time diaper for infant and child bed-wetters.

Machine Embodiment No. 6

Figure 17:
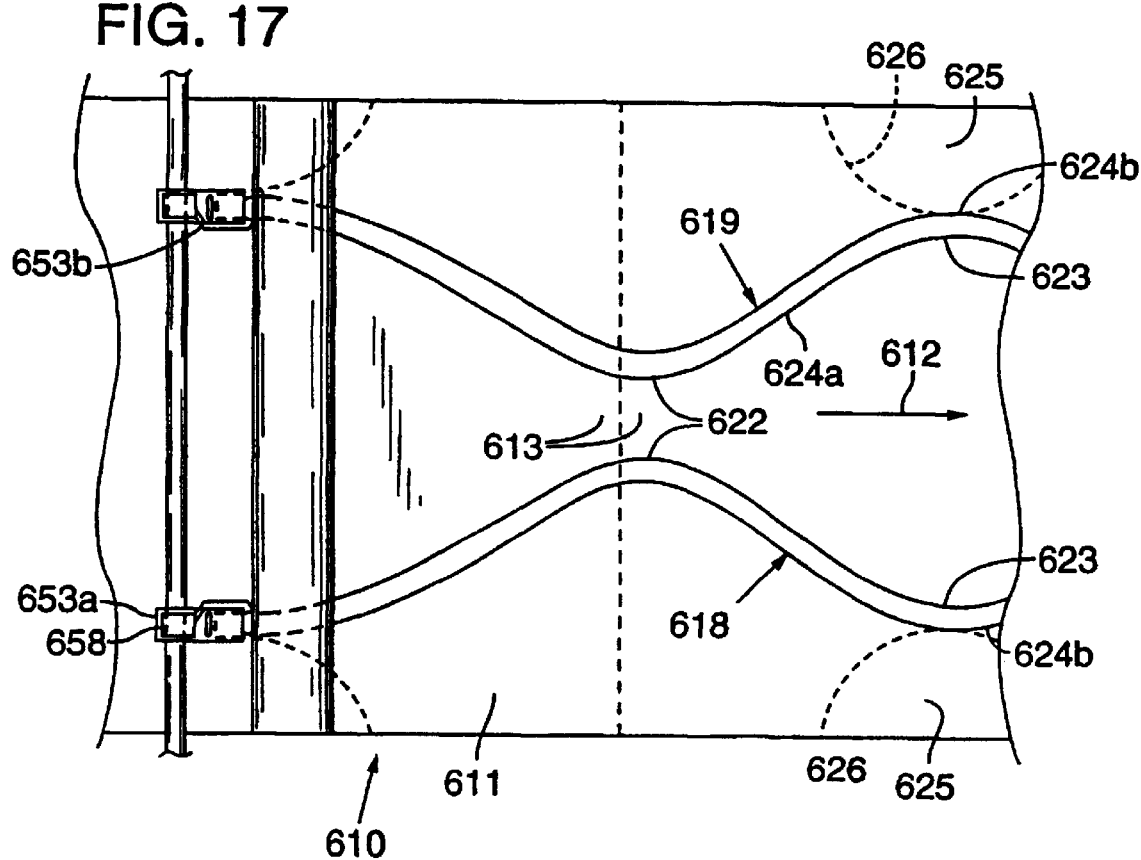
FIG. 17 is a top plan view of a machine for applying ribbon to a garment material according to another embodiment of the present invention.

FIG. 17 shows another embodiment of the present invention with reference numerals in the "600" series. The machine 610 produces a garment 601 (FIG. 18) in the "machine" direction wherein the garment is formed with the leg openings 626 oriented to the sides of machine flow path 612. Feeder heads 653a, 653b apply ribbons 618, 619 to the liner material 611 in a symmetric, sinuous repeating "hour-glass" contour. The hour-glass contour has narrow inboard regions 622 adjacent the garment waist regions 613 wherein the ribbons 618, 619 are closely spaced. The hour-glass contour has wide outboard regions 623 adjacent the leg openings 626 wherein the ribbons 618, 619 are widely spaced. The inboard edges 624a of the ribbons 618, 619 are adhered to the liner material 611 to form a raised barrier on the garment. The ribbons 618, 619 are not severed when the leg opening material 625 is severed by a die cutter, such as that shown in FIG. 2.

Figure 18:
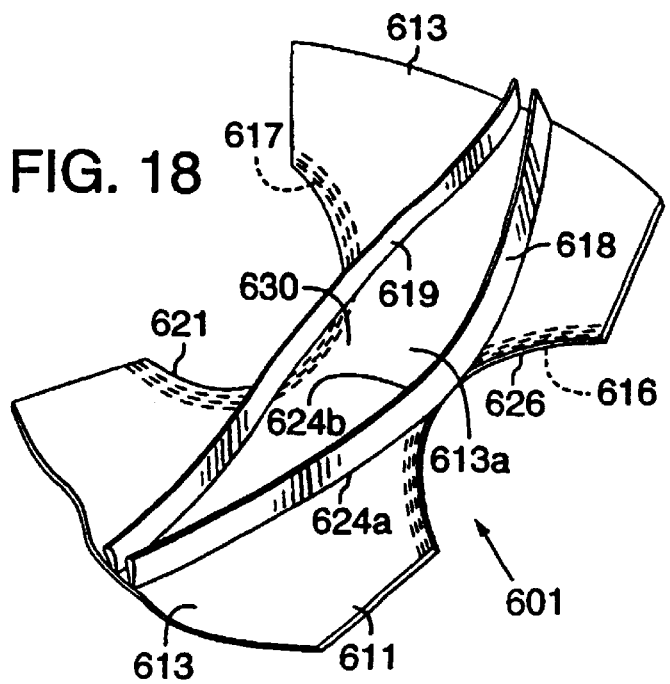
FIG. 18 is a perspective view of one form of disposable absorbent garment which may be produced by the machine shown in FIG. 17.

As shown in FIG. 18, the resulting ribbon barriers 618, 619 on the finished garment are positioned very close to the leg openings to provide a wide exudate containment region 630 in the crotch area 613a of the garment. Sets of elastic bands 616, 617 that elasticize the leg openings may be applied according to the teachings of the above-referenced patent application Ser. No. 08/493,425 of Thomas R. Herrmann.

Figure 19:
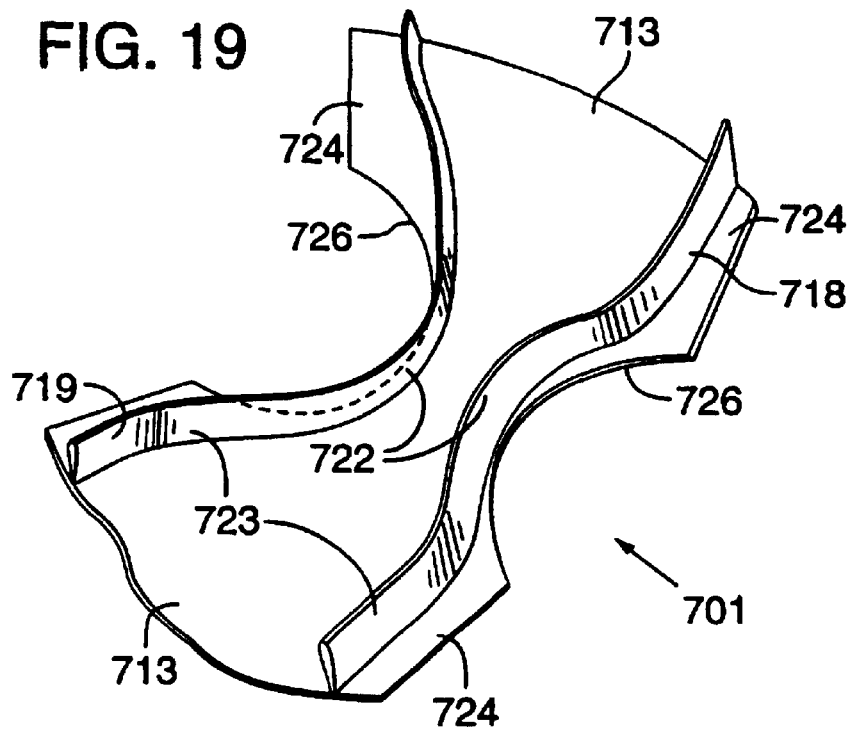
FIG. 19 is a perspective view of another form of disposable absorbent garment which may be produced by a modified version of the machine shown in FIG. 17.

The machine of FIG. 17 may be modified (by modification of a cam drive device like device 62a, 62b shown in FIG. 1) to produce a modified sinuous ribbon contour that yields the garment 701 of FIG. 19. Garment 701 has ribbons 718, 719 forming raised barriers with inboard portions 722 that curve along the leg openings 726, and outboard portions 723 that extend up the side regions 724 of the garment to the garment waist regions 713.

Machine Embodiment No. 7

Figure 20A:
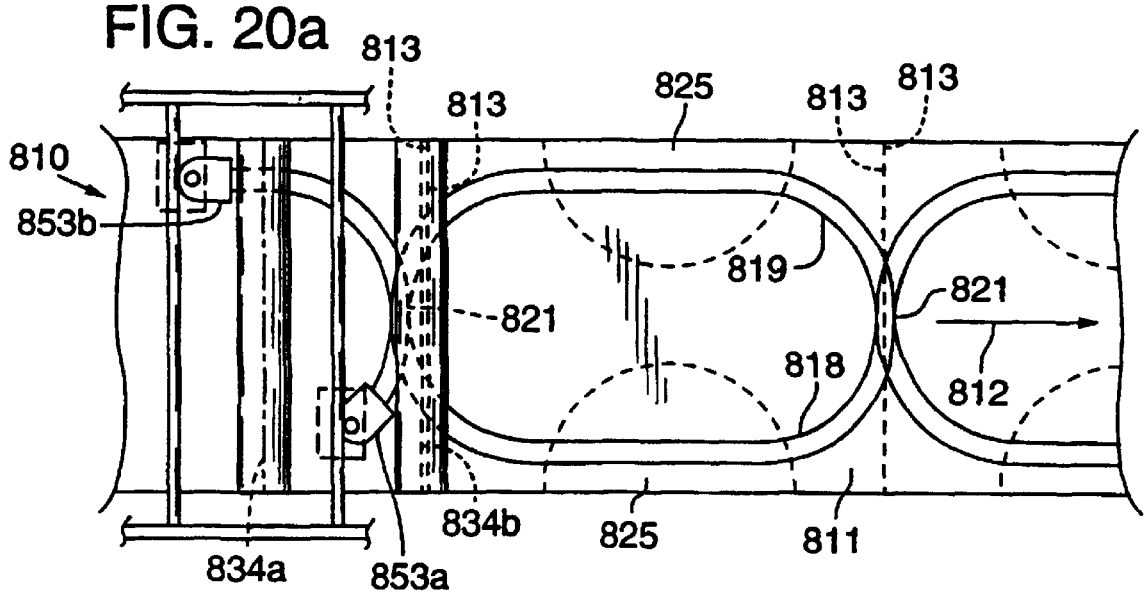
FIG. 20a is a top plan view of a machine for applying ribbon to a garment material according to one more embodiment of the present invention.

FIG. 20a shows another embodiment of the present invention with reference numerals in the "800" series. The machine 810 produces another garment 801 in the "machine" direction (FIG. 21), by using a staggered feeder head configuration much like that described relative to FIG. 8. In this embodiment, each rod-mounted feeder head 853a, 853b reciprocates nearly entirely across the liner material 811 being carried along flow path 812. The staggered feeder heads apply the ribbons 818, 819 to the liner material at respective nips 834a, 834b in overlapping sinuous contours resembling a repeating "figure-eight" contour.

In the illustrated figure-eight pattern, the ribbons intersect at 821 adjacent the intersection of the garment waist regions 813. The ribbons 818, 819 are applied steeply across the moving liner material adjacent the ribbon intersection 821, with an attending relatively high feeder head speed. Because of the high-speed steep ribbon application, pivotable heads 853a, 853b may be used to prevent the ribbon from tearing or folding over on itself during application adjacent the ribbon intersection.

Figure 20B:
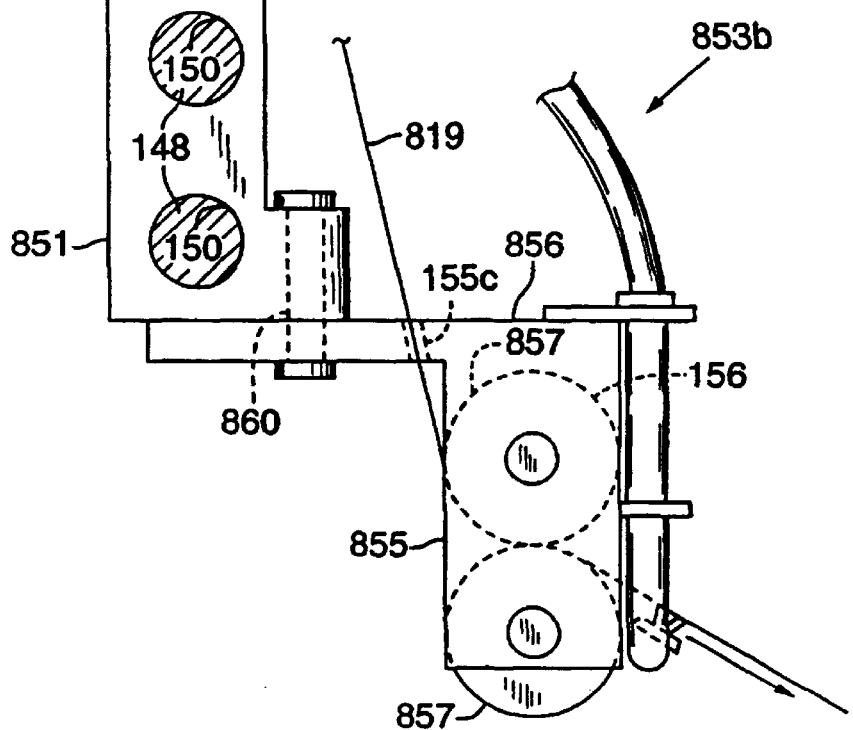

As best shown in FIG. 20b, pivotable feeder head 853b includes a rod-mounted slider block 851. A feeder bracket 855 has an upper base plate 856 that is pivotally mounted about a pivot shaft 860 that extends downwardly from the slider block 851. The feeder bracket 855 has a pair of feeder rollers 857 and is constructed much like the bracket 55 discussed relative to FIGS. 3 and 4.

The pivot connection permits the tension in the ribbon 819 to freely pivot the feeder bracket 855 as the feeder head moves across the flow path. As shown in FIG. 20a (feeder head 853a), such pivoting permits the ribbon to be guided straight from the rollers 857 no matter the steepness of the ribbon application across the flow path. It is also contemplated that such pivotal feeder heads may be used with any other of the machine embodiments described herein.

Figure 21:
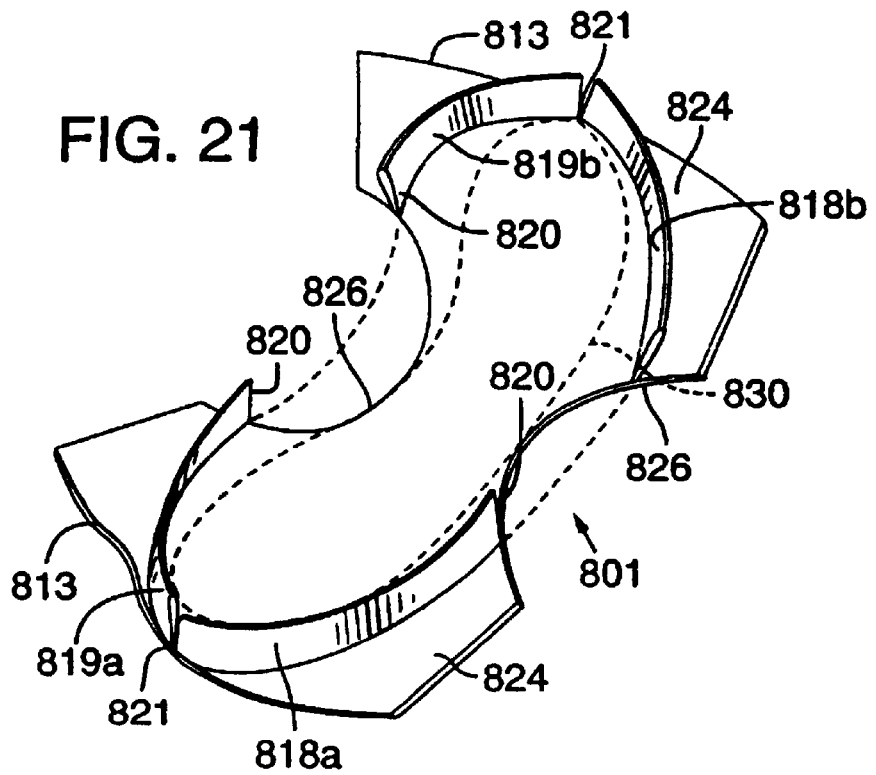

As best shown in FIGS. 20a and 21, the ribbons 818, 819 intersect at the garment waist regions 813, curve outwardly down the garment side portions 824, and extend generally linearly across the central portion of the leg opening material 825. The leg opening material 825 and the ribbon portions extending therealong are severed from the garment, producing the garment 801 with raised ribbon barriers 818a, 819a and 818b, 819b that respectively form inner leg gather and end cap barriers that extend in arched curves on the front and back of the garment. The arched ribbon barriers terminate at positions 820 at the front and back of the leg openings 826.

It is also contemplated that the stroke of the feeder heads 853a, 853b could be shortened such that the ribbons 818, 819 are applied straight along the garment inboard of the leg openings 825. The garment formed thereby has a substantially continuous oval containment pocket 830, the outline of which is designated by dashed line 830 in FIG. 21.

While all of the above embodiments describe the application of the ribbons upstream of the elastic band encasement, it is also contemplated that the ribbons may be applied to the liner sheet downstream of the elastic band encasement. In addition to adhesive fastening, the ribbons may be fastened to the liner by sewing, needlepunch, ultrasonics, heat melts, or other fastening means. Devices for accomplishing these types of fastening may be mounted on the ribbon feeder heads, or be mounted on separate structure on the machines to cooperate with the moving ribbon feeder heads. Furthermore, the present ribbon barriers may also be applied to garments with single composite material layer construction, such as disposable panties and the like.

While particular embodiments of the present invention have been illustrated and described herein, it should be obvious to those skilled in the art that variations and modifications are possible without departing from the spirit of the invention as set out in the appended claims.

I claim:

1. A disposable absorbent garment comprising:
    a front waist portion;
    a rear waist portion;
    a crotch portion positioned between said front and rear waist portions;
    a backsheet;
    a topsheet overlying said backsheet, said backsheet and said topsheet being shaped to form a pair of spaced-apart leg openings in said crotch portion;
    an absorbent core positioned between said topsheet and backsheet;
    a first elongate ribbon having a proximal edge and a distal edge with respect to said topsheet, and first and second ends, said first elongate ribbon being attached to said topsheet along said proximal edge in a curved pattern to form an arc extending toward said front waist portion; and
    a second elongate ribbon having a proximal edge and a distal edge with respect to said topsheet, and first and second ends, said second elongate ribbon being attached to said topsheet along said proximal edge in a curved pattern to form an arc extending toward said rear waist portion; wherein
    said first and second elongate ribbons comprise arc-shaped front and rear end caps for collecting and preventing the flow of waste.

2. The absorbent garment of claim 1, wherein said first and second ends of said first elongate ribbon terminate at respective said leg openings.

3. The absorbent garment of claim 1, wherein said first and second ends of said second elongate ribbon terminate at respective said leg openings.

4. The absorbent garment of claim 1, wherein said first and second ends of said second elongate ribbon extend through said crotch portion and terminate near said front waist portion.

5. The absorbent garment of claim 1, wherein said first and second ends of said elongate ribbons are coextensive to form a continuous flap-like barrier about the crotch portion of the garment.

6. The absorbent garment of claim 5, wherein said first and second elongate ribbons cooperatively form an oval-shaped containment region in said crotch portion of the garment.

7. The absorbent garment of claim 5, wherein said first elongate ribbon extends in the direction of said front waist portion to an extent greater than said second ribbon extends in the direction of said rear waist portion.

8. The absorbent garment of claim 5, wherein said second elongate ribbon extends in the direction of said rear waist portion to an extent greater than said first ribbon extends in the direction of said front waist portion.

9. The absorbent garment of claim 5, wherein said first and second ends of said second elongate ribbon extend through the crotch portion and terminate near said front waist portion.

10. The absorbent garment of claim 1, further comprising leg elastics positioned adjacent respective said leg openings.

11. The absorbent garment of claim 1, wherein said first and second elongate ribbons are elasticized at said distal edge thereof.

12. The absorbent garment of claim 1, further comprising elastic band members adhered to respective said distal edges of said first and second elongate ribbons.

13. The absorbent garment of claim 11, wherein said distal edges of said first and second elongate ribbons are folded to encase said respective elastic band members therein.

14. The absorbent garment of claim 1, wherein said first and second elongate ribbons extend in opposing arched curves which face the crotch portion of the absorbent garment, said elongate ribbons cooperatively defining a partial oval-shaped exudate containment region in said crotch portion of the garment.

15. The absorbent garment of claim 1, wherein said first elongate ribbon extends towards said front waist portion to a degree greater than said second elongate ribbon extends towards said rear waist portion.

16. The absorbent garment of claim 1, wherein said first and second elongate ribbons each have amplitudes with respect to said crotch portion, said first elongate ribbon having a greater amplitude than said second elongate ribbon.

17. The absorbent garment of claim 1, wherein said first and second elongate ribbons each have amplitudes with respect to said crotch portion, said second elongate ribbon having a greater amplitude than said first elongate ribbon.

18. The absorbent garment of claim 1, further comprising additional elongate ribbons positioned adjacent respective said first and second elongate ribbons.

19. The absorbent garment of claim 1, wherein said elongate ribbons comprise a non-woven fabric.

20. The absorbent garment of claim 19, wherein said first and second elongate ribbons comprise spun-bonded polypropylene.

21. The absorbent garment of claim 19, wherein said first and second elongate ribbons have two sides, one side comprising a polyethylene film and a second side comprising non-woven material.

22. The absorbent garment of claim 19, wherein said first and second elongate ribbons have an inner side facing the crotch portion and an outer side opposite said inner side, said inner side treated with a surfactant to render said inner side more hydrophilic with respect to said outer side.

23. The absorbent garment of claim 1, wherein said first and second elongate ribbons each have an inner side facing the crotch portion and an outer side opposite said inner side, said inner side comprising a polyethylene film and said outer side comprising a non-woven material.

24. The absorbent garment of claim 1, wherein said first and second elongate ribbons are about one inch thick as measured between said proximal edge and said distal edge.

* * * * *